United States Patent
Patel et al.

(10) Patent No.: US 10,056,159 B1
(45) Date of Patent: Aug. 21, 2018

(54) SYSTEM AND METHOD FOR MEDICAL RESOURCE UTILIZATION MANAGEMENT

(71) Applicant: MedPather, Inc., Austin, TX (US)

(72) Inventors: Mrigasha Patel, Minneapolis, MN (US); Ryan Egeland, Wayzata, MN (US); Brent Egeland, Austin, TX (US)

(73) Assignee: MedPather, Inc., Austin, TX (US)

( * ) Notice: Subject to any disclaimer, the term of this patent is extended or adjusted under 35 U.S.C. 154(b) by 0 days.

(21) Appl. No.: 15/885,621

(22) Filed: Jan. 31, 2018

(51) Int. Cl.
| | | |
|---|---|---|
| *G16H 40/20* | (2018.01) | |
| *G16H 10/60* | (2018.01) | |
| *H04L 12/26* | (2006.01) | |
| *G06N 5/02* | (2006.01) | |
| *H04L 12/66* | (2006.01) | |
| *G16H 40/40* | (2018.01) | |

(52) U.S. Cl.
CPC .............. *G16H 40/20* (2018.01); *G06N 5/02* (2013.01); *G16H 10/60* (2018.01); *G16H 40/40* (2018.01); *H04L 12/66* (2013.01); *H04L 43/10* (2013.01)

(58) Field of Classification Search
CPC ................................ G16H 40/20; G06F 17/60
See application file for complete search history.

(56) References Cited

U.S. PATENT DOCUMENTS

| | | | | |
|---|---|---|---|---|
| 2002/0165733 A1* | 11/2002 | Pulkkinen | ............. | G06F 19/321 705/2 |
| 2009/0048865 A1* | 2/2009 | Breazeale, Jr. | ........ | G06Q 10/00 705/2 |
| 2015/0310180 A1* | 10/2015 | Pattekar | ................ | G16H 40/20 705/2 |

OTHER PUBLICATIONS

"Survey of Wireless Indoor Positioning Techniques and Systems"; Liu et al.; IEEE Transaction on Systems, Man and Cybernetics, vol. 37, No. 6; Nov. 6, 2007 (Year: 2007).*

* cited by examiner

*Primary Examiner* — John A Pauls

(57) ABSTRACT

A gateway, a server, and a method are provided. The method includes receiving at least one message from a corresponding number of gateways, wherein each received message includes a first identification parameter associated with each gateway, and a second identification parameter associated with a beacon. The method also includes identifying a location the beacon is located, wherein the location is one location within an environment. The method further includes deriving a time duration that the beacon is located in the location. The method additionally includes determining a cost based on the time duration that the beacon is located in each location, wherein each location has a cost value associated with it.

3 Claims, 13 Drawing Sheets

SYSTEM AND METHOD FOR MEDICAL RESOURCE UTILIZATION MANAGEMENT

TECHNICAL FIELD

This disclosure relates generally to management of medical resources. More specifically, this disclosure relates to predictive modeling by tracking personnel, patients and equipment in a medical environment using beacons and a gateways, and generating a time based expenditure analysis based on the duration of time each of the tracked entities are within specific locations.

BACKGROUND

Each year, tens of millions of individuals seek or need the assistance of healthcare professionals and medical facilities. As such, healthcare is one of the largest industries in the country. However, the cost of healthcare is rising at an ever-increasing rate. Controlling and managing the rising cost of healthcare while providing quality medical care is a difficult equilibrium. Medical providers and facilities often struggle to provide quality care when the medical providers and facilities are not getting paid due to the increase in healthcare and medical expenses. As such, medical providers and medical facilities often struggle to predict the best allocation of resources as well as forecasting revenue, in order to provide quality care.

An ability to eliminate or reduce wasteful procedures while lowering overpriced services are often suggested to help reduce healthcare and medical expenses. Actuarial models of cost prediction, especially for healthcare, have typically not been as accurate or as helpful as desirable. Traditional actuarial methods of predicting medical costs are based on an economic model using standard demographic data (such as age and sex), and do not take actual real time data. Similarly, predictive modeling of medical resources based on actual use is not as helpful due to the numerous parts of in a hospital setting.

SUMMARY

This disclosure provides system and method for medical resource utilization management.

In one embodiment, a gateway is provided. The gateway includes a transceiver and a processor. The transceiver is configured to receive a ping from a beacon. The received ping includes an identification parameter associated with the beacon. The transceiver is also configured to transmit a message to a server when the ping is received. The processor is configured to derive a signal strength parameter associated with the received ping from the beacon directed towards a plurality of gateways. The processor is also configured to generate the message. The message includes the identification parameter associated with the beacon, a second identification parameter associated with the gateway, and the derived signal strength parameter.

In another embodiment, a server is provided. The server includes a transceiver. The transceiver is configured to receive at least one message from a corresponding number of gateways. Each received message includes a first identification parameter associated with each gateway, and a second identification parameter associated with a beacon. The server also includes a processor. The processor is configured to identify a location the beacon is located, wherein the location is one location within an environment. The processor is also configured to derive a time duration that the beacon is located in the location. The processor is further configured to determine a cost based on the time duration that the beacon is located in each location, wherein each location has a cost value associated with it.

In yet another embodiment a method is provided. The method includes receiving at least one message from a corresponding number of gateways, wherein each received message includes a first identification parameter associated with each gateway, and a second identification parameter associated with a beacon. The method also includes identifying a location the beacon is located, wherein the location is one location within an environment. The method further includes deriving a time duration that the beacon is located in the location. The method also includes determining a cost based on the time duration that the beacon is located in each location, wherein each location has a cost value associated with it.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 7-9B illustrate example user interface in accordance with embodiments of the present disclosure;

DETAILED DESCRIPTION

Figure 1:
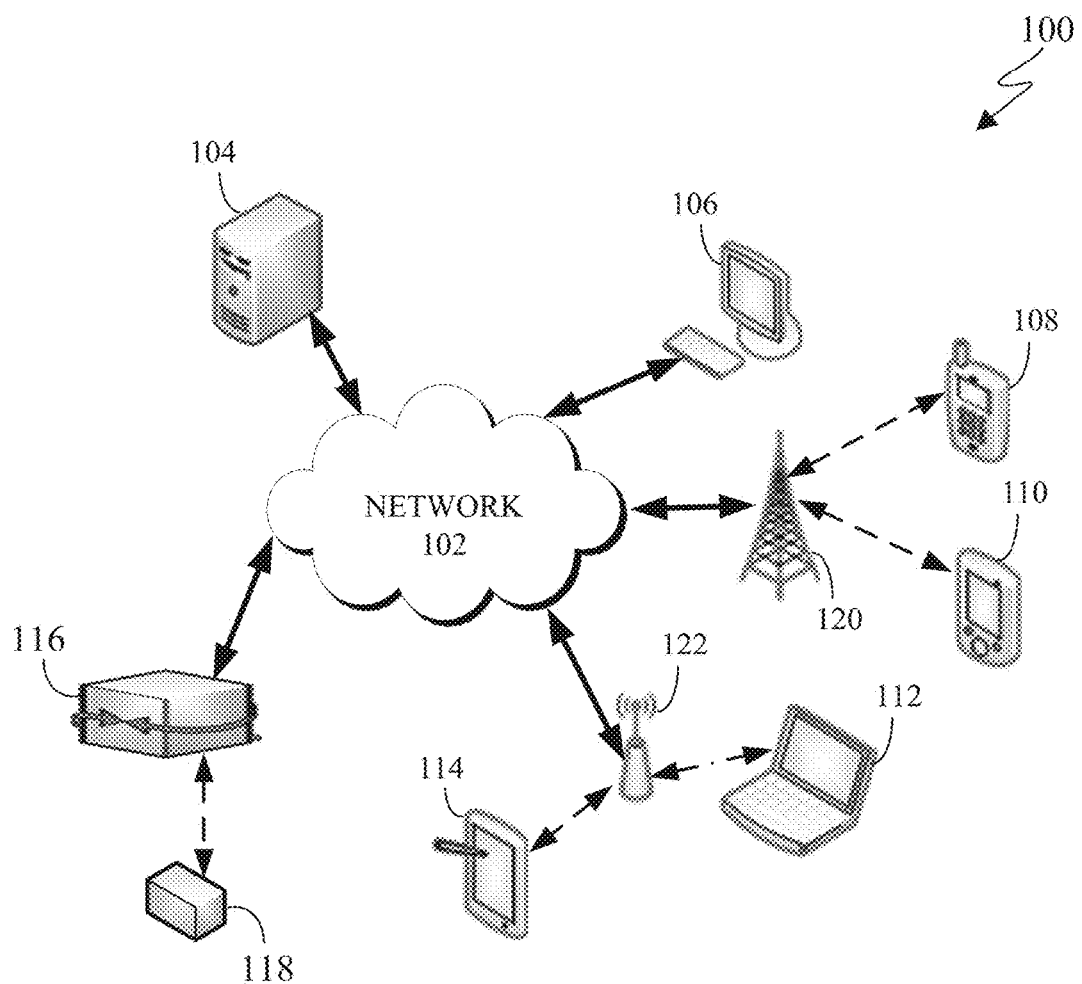
FIG. 1 illustrates an example communication system in accordance with embodiments of the present disclosure.

FIGS. 1 through 11, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably-arranged wireless communication system or device.

According to embodiments of the present disclosure, various methods for tracking individuals (such as patients and medical providers) and equipment are provided. In certain embodiments, beacons are carried by patients and medical providers and affixed to equipment. Gateways are located throughout a medical facility to receive pings from the beacons. For example, a beacon can be located in various rooms where patients typically are located, such as a waiting room, an exam room, a medical imaging room, a diagnostic testing room, an operating room, and the like.

According to embodiments of the present disclosure, various methods for deriving a cost associated with a particular location within a medical facility are provided. In certain embodiments, various rooms can have different costs associated with each room. For example, the cost associated with a waiting room is less than an exam room, while the cost associated with an exam room is less than a medical imaging room. The cost for a waiting room can be allocated based on the size of the room and the rent associated with the size as well as the value of the furniture in the room. The cost associated with an exam room can be allocated by the size of the room and the rent associated therewith as well as the cost of the equipment located in the room. In certain embodiments, the costs can also include the salary of the medical provider.

According to embodiments of the present disclosure, various methods for predictive modeling and management of medical resources are provided. In certain embodiments, methods for predictive modeling can include accumulating the costs each patient accrues during a visit to the medical facility. Based on the costs accrued, the medical facility is provided an understanding on the expected revenue. In certain embodiments, methods for predictive modeling can include analyzing expenditures and assigning resources to increase revenue. For example, if a specific room is not utilized to compensate for its costs, and another room is overused, then the predictive modeling can notify the medical facility.

Embodiments of the present disclosure provide for situations in which an electronic device, such as mobile device, can function as a beacon for a location to a gateway. For example, persons typically carry a mobile device, such as a smart phone, with them constantly. When the mobile device is in proximity to a gateway, the gateway can transmit a message to a server. The message indicates that a mobile device associated with a particular individual is within proximity to the gateway. The server can then derive the location of the mobile device and the individual to whom carries the mobile device. In certain embodiments, the gateway can also transmit a message when the beacon, such as a mobile device, is no longer in proximity to the gateway. This allows the server to derive a duration of time that the person was in a specific location.

FIG. 1 illustrates an example system 100 according to this disclosure. The embodiment of the system 100 shown in FIG. 1 is for illustration only. Other embodiments of the system 100 could be used without departing from the scope of this disclosure.

The system 100 includes network 102 that facilitates communication between various components in the system 100. For example, network 102 can communicate Internet Protocol (IP) packets, frame relay frames, Asynchronous Transfer Mode (ATM) cells, or other information between network addresses. The network 102 includes one or more local area networks (LANs), metropolitan area networks (MANs), wide area networks (WANs), all or a portion of a global network such as the Internet, or any other communication system or systems at one or more locations.

The network 102 facilitates communications between various server(s) 104 and various client devices 106-118. The client devices 106-118 may be, for example, a mobile device, a smart phone, a personal digital assistant (PDA) a tablet computer, a laptop, a personal computer, a wearable device; a tracking device (such as a beacon), a gateway device or a combination thereof.

Server 104 can represent one or more servers. Each server 104 includes any suitable computing or processing device that can provide computing services for one or more client devices. Each server 104 could, for example, include one or more processing devices, one or more memories storing instructions and data, and one or more network interfaces facilitating communication over the network 102. As described in more detail below with respect to FIGS. 2 and 4, the server 104 manages resources by receiving locations of beacons associated with persons and equipment.

Each client device 106-118 represents any suitable computing or processing device that interacts with at least one server or other computing device(s) over the network 102. In this example, the client devices 106-118 include a desktop computer 106, a mobile telephone or mobile devices 108 (such as a smartphone), a PDA 110, a laptop computer 112, a tablet computer 114, a gateway 116, and a beacon 118. However, any other or additional client devices could be used in the system 100.

In this example, some client devices 108-118 communicate indirectly with the network 102. For example, the client devices 108 and 110 (mobile devices 108 and PDA 110, respectively) communicate via one or more base stations 120, such as cellular base stations or eNodeBs (eNBs). Also, the client devices 112, 114, and 116 (laptop computer, tablet computer, gateway respectively) communicate via one or more wireless access points 122, such as IEEE 802.11 wireless access points. In certain embodiments, gateway 116 communicates directly with network 102 instead of through wireless access point 122. Beacon 118 communicates with network 102 through the gateway 116. In certain embodiments, the beacon 118 communicates with the gateway 116 through a short range frequency communication channel such as BLUETOOTH, WI-FI, or radio frequency identification (RFID). Note that these are for illustration only and that each client device 106-118 could communicate directly with the network 102 or indirectly with the network 102 via any suitable intermediate device(s) or network(s).

In certain embodiments, the mobile device 108 (or any other client device 106-118) can transmit information securely and efficiently to another device, such as, for example, the server 104. The gateway 116 (or any other client device 106-118) can trigger the information transmission between itself and the server 104. In certain embodiments, mobile device 108, laptop computer 112, or tablet computer 114 can function as a beacon 118 or a gateway 116.

Although FIG. 1 illustrates one example of a system 100, various changes can be made to FIG. 1. For example, the system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

The processes and systems provided in this disclosure allow for the beacon 118, or the gateway 116, to provide location information of an individual or equipment. In certain embodiments, the beacon 118 is affixed to an individual or a piece of equipment. The gateway 116 ascertains location information from the beacon 118 and transmits a message to the server 104 to indicate indicates the location of the beacon 118.

Figure 2:
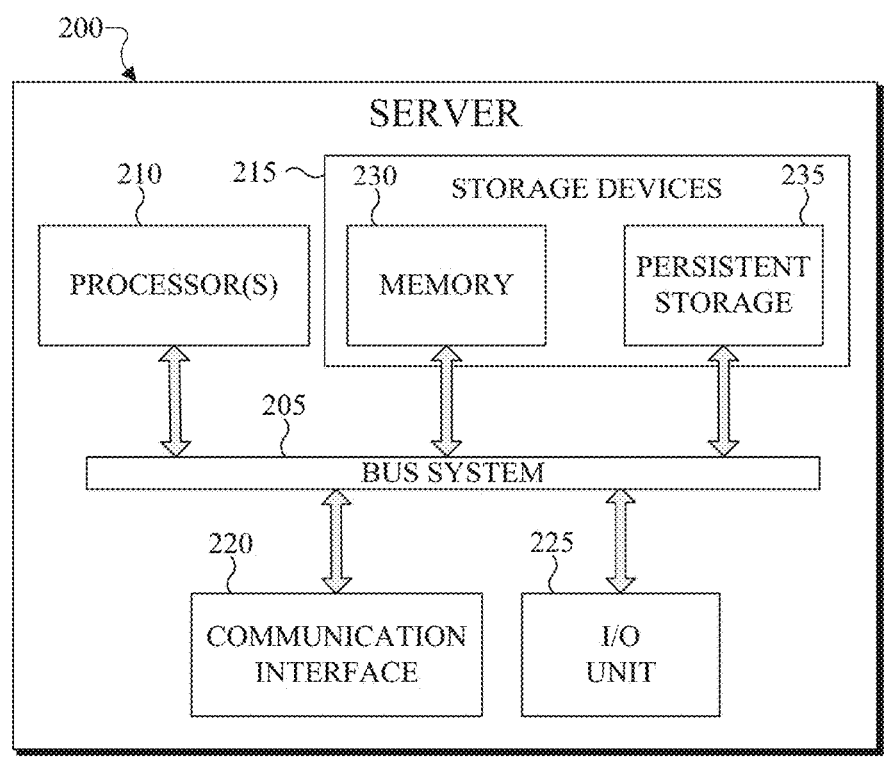
FIG. 2 illustrates an example server device in accordance with embodiments of the present disclosure.
Figure 3:
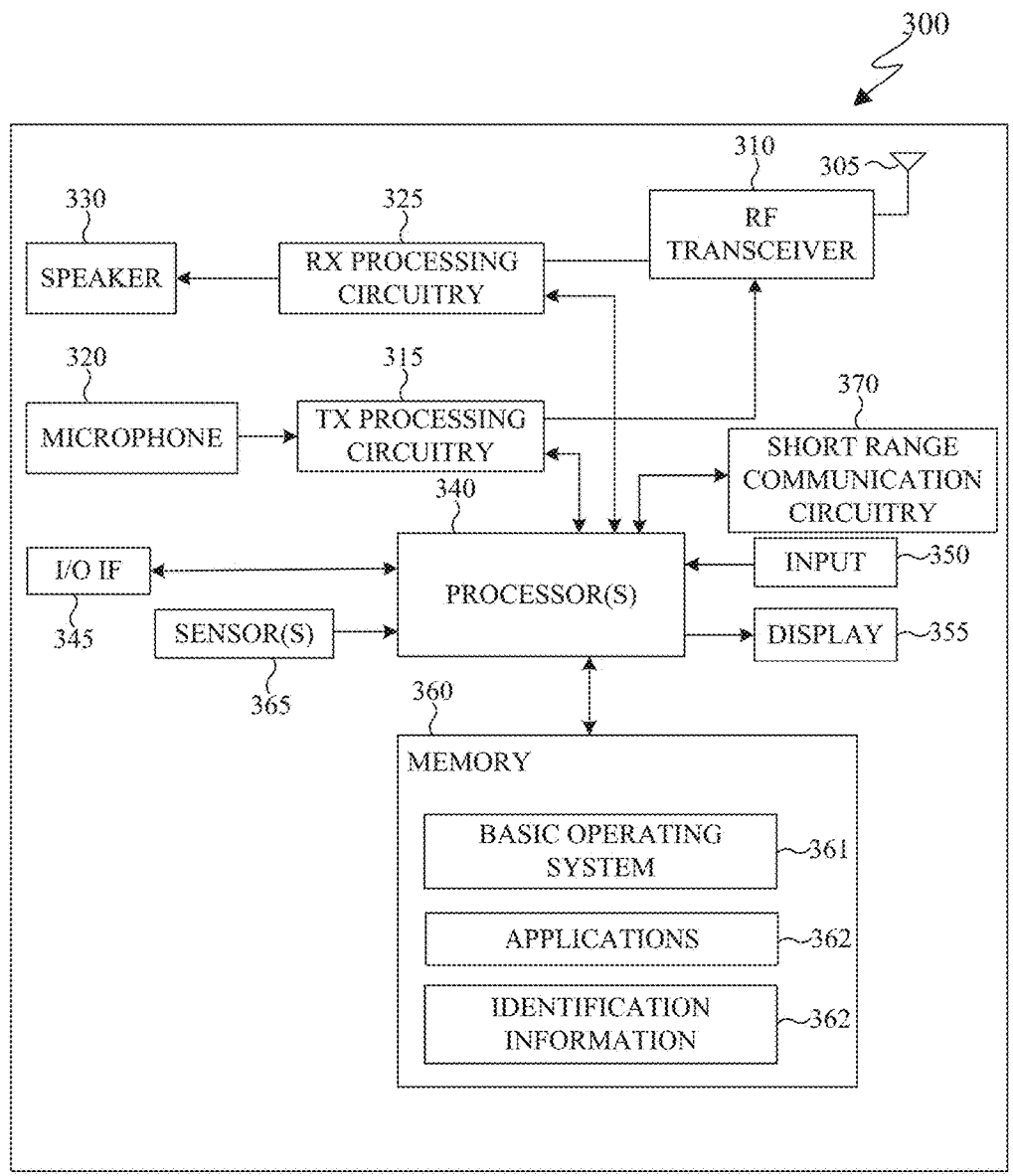
FIG. 3 illustrates an example electronic device in accordance with embodiments of the present disclosure.

FIGS. 2 and 3 illustrate example devices in a computing system in accordance with an embodiment of this disclosure. In particular, FIG. 2 illustrates an example server 200, and FIG. 3 illustrates an example electronic device 300. The server 200 could represent the server 104 in FIG. 1, and the electronic device 300 could represent one or more of the client devices 106-118 in FIG. 1.

Server 200 can represent one or more local servers, one or more location servers, or one or more predictive cost analysis server. As shown in FIG. 2, the server 200 includes a bus system 205 that supports communication between at least one processor(s) 210, at least one storage device(s) 215, at least one communications interface 220, and at least one input/output (I/O) unit 225.

The processor 210 executes instructions that can be stored in a memory 230. The processor 210 can include any suitable number(s) and type(s) of processors or other devices in any suitable arrangement. Example types of processor(s) 210 include microprocessors, microcontrollers, digital signal processors, field programmable gate arrays, application specific integrated circuits, and discreet circuitry.

The memory 230 and a persistent storage 235 are examples of storage devices 215 that represent any structure(s) capable of storing and facilitating retrieval of information (such as data, program code, or other suitable information on a temporary or permanent basis). The memory 230 can represent a random access memory or any other suitable volatile or non-volatile storage device(s). The persistent storage 235 can contain one or more components or devices supporting longer-term storage of data, such as a ready only memory, hard drive, Flash memory, or optical disc.

The communications interface 220 supports communications with other systems or devices. For example, the communications interface 220 could include a network interface card or a wireless transceiver facilitating communications over the network 102. The communications interface 220 can support communications through any suitable physical or wireless communication link(s).

The I/O unit 225 allows for input and output of data. For example, the I/O unit 225 can provide a connection for user input through a keyboard, mouse, keypad, touchscreen, or other suitable input device. The I/O unit 225 can also send output to a display, printer, or other suitable output device.

Note that while FIG. 2 is described as representing the server 104 of FIG. 1, the same or similar structure could be used in one or more of the various client devices 106-118. For example, a desktop computer 106 or a laptop computer 112 could have the same or similar structure as that shown in FIG. 2.

FIG. 3 illustrates an electronic device 300 in accordance with an embodiment of this disclosure. The embodiment of the electronic device 300 shown in FIG. 3 is for illustration only and other embodiments could be used without departing from the scope of this disclosure. The electronic device 300 can come in a wide variety of configurations, and FIG. 3 does not limit the scope of this disclosure to any particular implementation of an electronic device. In certain embodiments, one or more of the client devices 106-118 of FIG. 1 can include the same or similar configuration as electronic device 300.

Electronic device 300 is a location acquisition, and tracking device used in detecting a location of objects and persons within an environment. In certain embodiments, electronic device 300 is useable with data transfer applications, such receiving a ping and transmitting a message. The electronic device 300 can be a mobile communication device, such as, for example, a wireless terminal, a desktop computer (similar to desktop computer 106 of FIG. 1), a mobile device (similar to mobile device 108 of FIG. 1), a PDA (similar to PDA 110 of FIG. 1), a laptop (similar to laptop computer 112 of FIG. 1), a tablet (similar to tablet computer 114), a gateway (similar to the gateway 116 of FIG. 1), a beacon (similar to the beacon 118 of FIG. 1) and the like.

As shown in FIG. 3, the electronic device 300 includes an antenna 305, a radio frequency (RF) transceiver 310, a transmit (TX) processing circuitry 315, a microphone 320, and a receive (RX) processing circuitry 325. In certain embodiments, the RF transceiver 310 is a communication unit that includes a BLUETOOTH transceiver, a WI-FI transceiver, ZIGBEE, infrared, and the like. The electronic device 300 also includes a speaker 330, a processor 340, an input/output (I/O) interface 345, an input 350, a display 355, a memory 360, and a sensor(s) 365. The memory 360 includes an operating system (OS) 361, applications 362, and identification information 363.

The RF transceiver 310 receives, from the antenna 305, an incoming RF signal transmitted such as a BLUETOOTH or WI-FI signal from an access point (such as a base station, WI-FI router, BLUETOOTH device) of the network 102 (such as a WI-FI, BLUETOOTH, cellular, 5G, LTE, LTE-A, WiMAX, or any other type of wireless network). The RF transceiver 310 can down-convert the incoming RF signal to generate an intermediate frequency or baseband signal. The intermediate frequency or baseband signal is sent to the RX processing circuitry 325 that generates a processed baseband signal by filtering, decoding, or digitizing the baseband or intermediate frequency signal, or a combination thereof. The RX processing circuitry 325 transmits the processed baseband signal to the speaker 330 (such as for voice data) or to the processor 340 for further processing (such as for web browsing data and remittance).

The TX processing circuitry 315 receives analog or digital data from the microphone 320 or other outgoing baseband data from the processor 340. The outgoing baseband data can include a message, web data, e-mail, or interactive video game data. The TX processing circuitry 315 encodes, multiplexes, digitizes, or a combination thereof, the outgoing baseband data to generate a processed baseband or intermediate frequency signal. The RF transceiver 310 receives the outgoing processed baseband or intermediate frequency signal from the TX processing circuitry 315 and up-converts the baseband or intermediate frequency signal to an RF signal that is transmitted via the antenna 305.

The processor 340 can include one or more processors or other processing devices and execute the OS 361 stored in the memory 360 in order to control the overall operation of the electronic device 300. For example, the processor 340 could control the reception of forward channel signals and the transmission of reverse channel signals by the RF transceiver 310, the RX processing circuitry 325, and the TX processing circuitry 315 in accordance with well-known principles. The processor 340 is also capable of executing other applications 362 resident in the memory 360, such as, one or more applications generating a message or deriving a received signal strength or the like.

The processor 340 can execute instructions that are stored in a memory 360. The processor 340 can include any suitable number(s) and type(s) of processors or other devices in any suitable arrangement. For example, in some embodiments, the processor 340 includes at least one microprocessor or microcontroller. Example types of processor 340 include microprocessors, microcontrollers, digital signal processors, field programmable gate arrays, application specific integrated circuits, and discreet circuitry The processor 340 is also capable of executing other processes and programs resident in the memory 360, such as operations that receive, store, and timely instruct by providing location detection and remote tracking capabilities and processing. The processor 340 can move data into or out of the memory 360 as required by an executing process. In some embodiments, the processor 340 is configured to execute plurality of applications 362 based on the OS 361 or in response to signals received from eNBs or an operator. In certain embodiments, the processor 340 is configured to instruct memory 360 to store identification information associated with the electronic device 300 or previous location information received from a beacon in an information repository, or both. The processor 340 is also coupled to the I/O interface 345 that provides the electronic device 300 with the ability to connect to other devices, such as client devices 106-118. The I/O interface 345 is the communication path between these accessories and the processor 340.

The processor 340 is also coupled to the input 350 and the display 355. The operator of the electronic device 300 can use the input 350 to enter data or inputs into the electronic device 300. Input 350 can be a keyboard, touch screen, mouse, track ball, voice input, or other device capable of acting as a user interface to allow a user in interact with electronic device 300. For example, the input 350 can include voice recognition processing thereby allowing a user to input a voice command via microphone 320. For another example, the input 350 can include a touch panel, a (digital) pen sensor, a key, or an ultrasonic input device. The touch panel can recognize, for example, a touch input in at least one scheme among a capacitive scheme, a pressure sensitive scheme, an infrared scheme, or an ultrasonic scheme. Input 350 can be associated with sensor(s) 365 and/or a camera by providing additional input to processor 340. In certain embodiments, sensor 365 includes inertial sensors (such as, accelerometers, gyroscope, and magnetometer), optical sensors, motion sensors, cameras, pressure sensors, heart rate sensors, altimeter, and the like. The input 350 can also include a control circuit. In the capacitive scheme, the input 350 can recognize touch or proximity. The display 355 can be a liquid crystal display (LCD), light-emitting diode (LED) display, optical LED (OLED), active matrix OLED (AMOLED), or other display capable of rendering text and/or graphics, such as from websites, videos, games, images, and the like. In certain embodiments, electronic device 300 does not include input 350 or display 355 or both.

Processor 340 can also be connected to a short range communication circuitry 370. The short range communication circuitry 370 can include additional communication interfaces, such as BLUETOOTH, ZIGBEE, infrared, and the like. In certain embodiments, short range communication circuitry 370 can be a part of the processing circuitry 325 and 315. In certain embodiments, the short range communication circuitry 370 includes Near Field Communication (NFC). NFC can wirelessly transmit and receive data with other NFC devices. In one example, the NFC can be used to transmit or receive, a ping from a beacon. The NFC can emit and/or receive a predetermined Radio Frequency (RF) within a predetermined region. The NFC service may include, for example, a terminal mode, a card mode (or NFC card mode), and a Peer-To-Peer (P2P) mode. The terminal mode executes a function of receiving a ping.

The memory 360 is coupled to the processor 340. Part of the memory 360 could include a random access memory (RAM), and another part of the memory 360 could include a Flash memory or other read-only memory (ROM).

The memory 360 can include persistent storage (not shown) that represents any structure(s) capable of storing and facilitating retrieval of information (such as data, program code, and/or other suitable information on a temporary or permanent basis). The memory 360 can contain one or more components or devices supporting longer-term storage of data, such as a ready only memory, hard drive, Flash memory, or optical disc. The memory 360 also can contain identification information 363 that includes identification information of the electronic device 300 and an identification parameter of another electronic device similar to the electronic device 300, such as a beacon. Identification information 363 can also contain data received from a beacon. Identification information 363 can include an identification number a room number, a geographic location, and the like.

Electronic device 300 further includes one or more sensor(s) 365 that can meter a physical quantity or detect an activation state of the electronic device 300 and convert metered or detected information into an electrical signal. In certain embodiments, sensor 365 includes inertial sensors (such as accelerometers, gyroscopes, and magnetometers), optical sensors, motion sensors, cameras, pressure sensors, heart rate sensors, altimeter, and the like. For example, sensor 365 can include one or more buttons for touch input, (such as on a headset or the electronic device 300), a camera, a gesture sensor, a gyroscope or gyro sensor, an air pressure sensor, a magnetic sensor or magnetometer, an acceleration sensor or accelerometer, a proximity sensor, a color sensor, a bio-physical sensor, a temperature/humidity sensor, an illumination sensor, an Ultraviolet (UV) sensor, an Electromyography (EMG) sensor, an Electroencephalogram (EEG) sensor, an Infrared (IR) sensor, an ultrasound sensor, an iris sensor, a fingerprint sensor, and the like. The sensor 365 can further include a control circuit for controlling at least one of the sensors included therein. The sensor(s) 365 can be used to determine an orientation and facing direction, as well as geographic location of the electronic device 300. Any of these sensor(s) 365 can be located within the electronic device 300 or another electronic device in communication with the electronic device 300.

Although FIGS. 2 and 3 illustrate examples of devices in a computing system, various changes can be made to FIGS. 2 and 3. For example, various components in FIGS. 2 and 3 could be combined, further subdivided, or omitted and additional components could be added according to particular needs. As a particular example, the processor 340 could be divided into multiple processors, such as one or more central processing units (CPUs) and one or more graphics processing units (GPUs). In addition, as with computing and communication networks, electronic devices and servers can come in a wide variety of configurations, and FIGS. 2 and 3 do not limit this disclosure to any particular electronic device or server.

Figure 4:
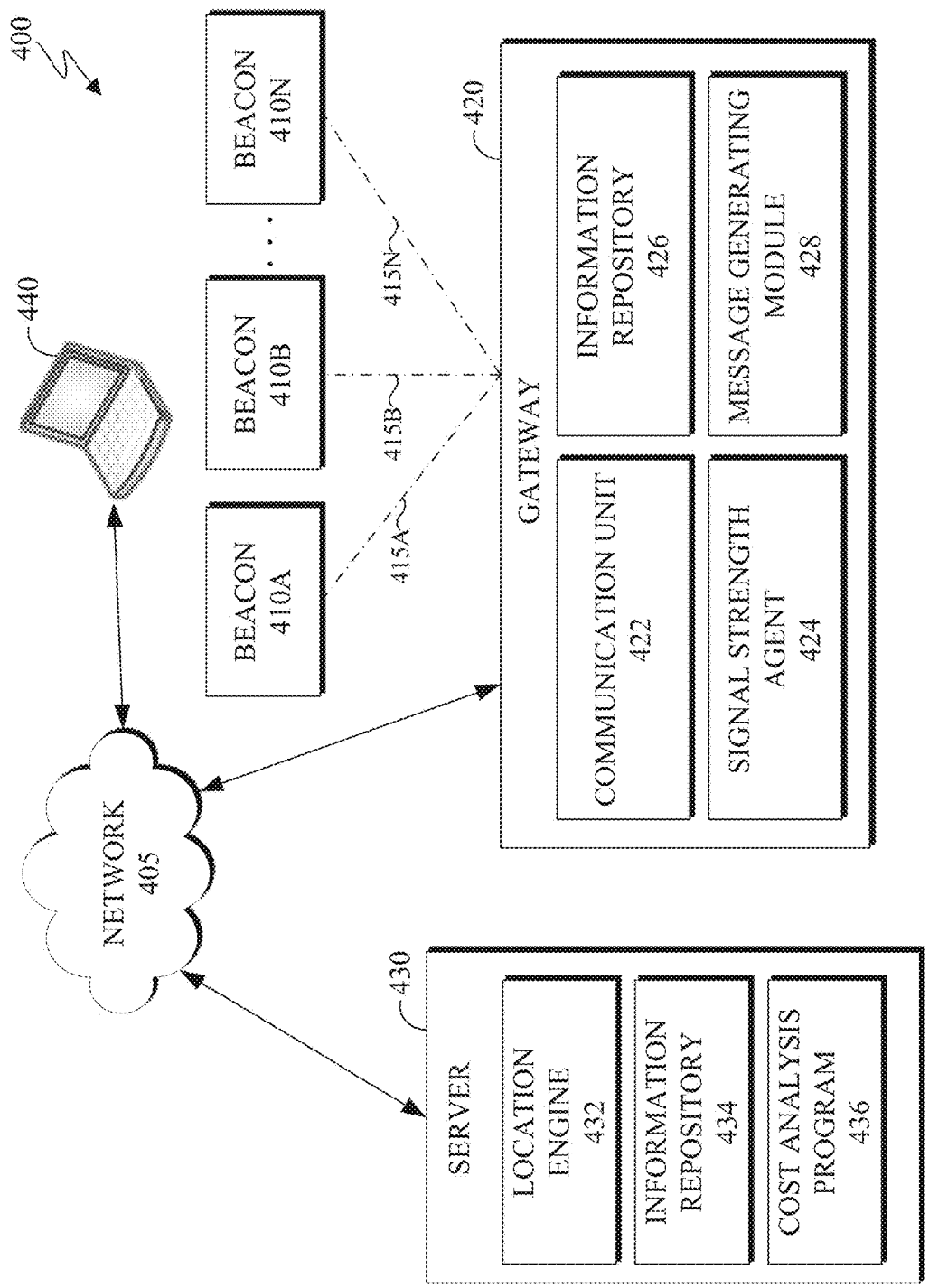
FIG. 4 illustrates an example block diagram in accordance with embodiments of the present disclosure.

FIG. 4 illustrates an example block diagram in accordance with embodiments of the present disclosure. The embodiment of the system architecture 400 shown in FIG. 4 is for illustration only. Other embodiments could be used without departing from the scope of the present disclosure.

System architecture 400 illustrates a high-level overview of an embodiment of the present disclosure to track beacon location and derive a cost based analysis based on a beacon's location over network 405. System architecture 400 includes beacon 410A, beacon 410B, through beacon 410N (hereinafter collectively referred to as beacon 410A-N), in communication with a gateway 420 over short range communication ping 415A, 415B through 415N, respectively (hereinafter collectively referred to as ping 415A-N). System architecture 400 also includes the gateway 420, a server 430, and a computer 440 in communication over network 405.

Network 405 can be configured similar to network 102 of FIG. 1. Server 430 can be configured similar to server 104 of FIG. 1, and server 200 of FIG. 2. Beacon 410A-410N can be configured similar to any of the one or more client devices 106-118 of FIG. 1 (such as the beacon 118), and can include internal components similar to that of electronic device 300 of FIG. 3. Gateway 420 can be configured similar to any of the one or more client devices 106-118 of FIG. 1 (such as the gateway 116) and can include internal components similar to that of the electronic device 300 of FIG. 3.

Network 405 is used to provide communication between the gateway 420, the server 430, and the computer 440. Network 405 can be a short range communication network, personal area network (PAN), Local Area Networks (LANs), Wireless Local Area Networks (WLANs), the Internet, the Public Switched Telephone Network (PSTN), WAN such as public cellular service as well as other wireless networks. Network 405 may also be the Internet, representing a worldwide collection of networks and gateways that use Transmission Control Protocol/Internet Protocol (TCP/IP) protocols to communicate with one another. Network 405 can include a variety of connections, such as, wired, wireless or fiber optic connections Beacon 410A-N represents any number of beacons used to track individuals and assets. In certain embodiments, individuals include patients, medical providers, and staff. In certain embodiments, assets include mobile medical equipment. Each beacon 410A-N, such as 410A, is configured to be affixed to an individual or an asset for tracking and monitoring the location of the individual or asset. Each beacon 410A-N can transmit a ping that is received by the gateway 420. The ping is a short range communication burst that includes the identification information such as an identification parameter of the beacon that transmitted the ping. For example, the gateway 420 can identify when a specific beacon is near, such as beacon 410A, based on the identification parameter that is included in the ping from the beacon 410A. For example, each beacon 410A-N can transmit a respective signal, such as a ping 415A-N. In certain embodiments, each beacon 410A-N can include a power source such as a battery.

In certain embodiments, beacon 410A-N can be affixed to an asset, such as a portable medical device. In certain embodiments, beacon 410A-N can be associated with an individual. For example, beacon 410A can be affixed to the badge of a medical provider, while beacon 410B is affixed to a wristband worn by a patient. Beacon 410B can be a sticker attached to the wristband. In another example, beacon 410C can be associated with a mobile device of a user, such as a smart phone.

In certain embodiments, each beacon 410A-N includes a communication unit configured to transmit a short range communication such as NFC, BLUETOOTH, RFID and the like. In certain embodiments, each beacon 410A-N includes a RFID tag, where the RFID reader can be the gateway 420. The RFID tag can be passive, active, or battery-assisted passive. For example, an active tag has an on-board battery and periodically transmits its identification parameter via a signal such as pings 415A-N. A battery-assisted passive tag has a small battery on board and is activated when in the presence of an RFID reader. A passive tag includes no battery; rather, the tag uses the radio energy transmitted by the reader. When the tag is in range of an RFID reader, the tag can transmit the identification parameter of the respective beacon.

In certain embodiments, each beacon is configured to transmit the ping 415A-N at predetermined time intervals. In certain embodiments, each beacon is configured to transmit the ping 415A-N when each beacon is within proximity to the gateway 420.

Beacon 410A-N is configured for one way or two way communication. If beacon 410A-N is configured for one-way communication, then each beacon 410A-N transmits the identification parameter in a signal such as ping 415A-N respectively. If beacon 410A-N is configured for two-way communication, then each beacon 410A-N transmits the identification parameter in a signal such as ping 415A-N respectively, as well as capable of receiving instructions from the gateway 420. The instructions can change parameters and configurations of the particular beacon. For example, instructions can include one or more: (i) post configuration changes; (ii) maintenance tasks; (iii) instructions to perform a self-diagnostic test and transmit the results; (iv) re-flash the beacons with a set of new firmware, such that the a particular beacon 410A-N is firmware-over-the-air capable, and the like. It is noted that a portion of the beacons 410A-N can be configured for one-way communication, while another portion of the beacons 410A-N can be configured for two-way communication.

In certain embodiments, each beacon 410A-N has two states: a dormant state and an active state. In the dormant state, each beacon 410A-N is powered down to reserve power. In the active state, each beacon 410A-N transmits the signal such as ping 415A-N to a gateway, such as the gateway 420.

In certain embodiments, beacon 410A-N can also transmit a status parameter. The status parameter indicates whether the beacon is associated with a patient or a staff member. If the beacon is associated with a patient, the status parameter can include a confidential value that is associated with the patient. If the beacon is associated with a staff member such as a medical provider, medical technician, and the like, then the status parameter can include information associated with the staff member. A medical provider can include a doctor, a nurse, a physician's assistant, a nurse practitioner, a pharmacist, a therapist such as a physical therapist, an occupational therapist, a respiratory therapist, a speech therapist, and the like. Each staff member may have a unique salary that is associated with the cost analysis program 436 or maintained in information repository 434 or both.

Gateway 420 represents one or more electronic devices that can be used to communicate with each beacon 410A-N via ping 415A-415N and the server 430. Although system architecture 400 only illustrates a single gateway 420, it is noted that multiple gateways can be utilized.

In certain embodiments, the gateway 420 is located in a stationary position with a structure such as a hospital building, a medical facility, medical provider's office, and the like. Each gateway 420 can be located in a predetermined location within the structure. For example, each room within the structure can include a gateway. An example environment illustrating a structure with a plurality of gateways, such as gateway 420, is depicted below with respect to FIG. 6. In certain embodiments, the gateway 420 is mobile Each gateway 420 serves as a receiver of a ping, such as ping 415A-N, for tracking each beacon 410A-N. Each gateway 420 can generate and transmit a message to the server 430, indicating the location of each beacon 410A-N. For example, when the gateway 420 receives a ping, such as ping 415A, the gateway can generate a message and transmit the message to the server 430, over network 405. The gateway 420 includes a communication unit 422, a signal strength agent 424, an information repository 426, and a message generating module 428.

The communication unit 422 of the gateway 420 provides for both short range communication and long range communication. For example, the communication unit 422 provides communication between the gateway 420, the server 430, as well as each beacon 410A-N. In certain embodiments, the gateway 420 is configured for two-way communication. For example, the gateway 420 can receive a ping 415A-N from each beacon 410A-N and transmit a generated message to the server 430. The gateway 420 is also capable of receiving instructions from the server 430. In certain embodiments, the gateway 420 can receive instructions from the server 430 and forward the received instructions to one or more beacons such as beacon 410A. In certain embodiments, the communication unit 422 can be an RFID reader. In certain embodiments, the communication unit 422 can include short range communication circuity (similar to short range communication circuity 370 of FIG. 3) such as BLUETOOTH, NFC, ZIGBEE, and the like. Communication unit 422 can also include components that provide for communication to the internet or a private network or both, through WI-FI.

In certain embodiments, ping 415A, between the beacon 410A and the gateway 420, represents a short range communication. Ping 415A occurs when the beacon 410A is in proximity to the gateway 420. For example, the beacon 410A can be located within a predefined distance from the gateway 420 allowing communication of occur between the beacon 410A and the gateway 420. Ping 415A can also occur when the gateway 420 transmits received instructions or from server 430, such as configuration changes.

Signal strength agent 424 derives a signal strength parameter associated a received ping, such as pings 415A-N. For example, signal strength agent 424 measures the power present in s received radio signal of a received ping, such as ping 415A. The derived signal strength parameter provides a value as to the distance the beacon 410A is from the gateway 420. For example, when multiple gateways are located in close proximity, it is possible for more than one gateway to receive the ping 415A from beacon 410A. Therefore, each signal strength agent 424 can derive the signal strength parameter that indicates an approximate distance the beacon 410A is from each gateway. Based on the strength parameter, the server 430 can identify the location of the beacon based on which signal strength parameter is stronger. That is, when the server 430 receives a message from multiple gateways, the server 430 can identify the location of the beacon 410A as the location of a specific gateway based on identifying which signal strength parameter from a particular gateway is the strongest. This example is discussed further with reference to FIG. 5, below.

The information repository 426 represents any structure(s) capable of storing and facilitating retrieval of information (such as data, program code, or other suitable information on a temporary or permanent basis). The information repository 426 is capable of saving location information received from ping 415A-N. In certain embodiments, the information repository 426 is capable of saving location information associated with each beacon 410A-N that gateway 420 communicates with. The information repository 426 maintains an identification parameter associated with the gateway 420. For example, in a structure (such as a hospital building, a medical facility, medical provider's office, and the like) that includes multiple gateways, the identification parameter associated with each gateway corresponds to a location within the structure. In certain embodiments, the identification parameter associated with the gateway 420 is the actual location within the structure. In certain embodiments, the identification parameter associated with the gateway 420 is a variable that corresponds to a look-up table associated with the server 430.

Message generating module 428 generates a message in response to the gateway 420 receiving a ping, such as ping 415A. Message generating module 428 generates a message that includes the identification parameter of the beacon that transmitted the received ping. For example, when beacon 410A transmits ping 415A, the gateway 420 receives identification parameter of the beacon 410A. Once the gateway 420 receives identification parameter of the beacon 410A, the message generating module 428 generates a message that includes the identification parameter of the beacon 410A and the identification parameter of the gateway 420. In certain embodiments, the message also includes a time stamp of the received ping 415A.

In certain embodiments, the message generating module 428 is capable of reducing the number of messages the gateway 420 transmits. That is, if the beacon 410A repeats a broadcast every time it is in proximity to the gateway 420, or the beacon 410A repeats a broadcast at a predetermined interval, the message generating module 428 can prevent the communication unit 422 of the gateway 420 from transmitting a message each time the gateway 420 receives the ping 415A from beacon 410A. For example, the message generating module 428 can employ an age criteria, such as a time window, to reduce the number of transmission by the gateway 420. A time window limits the number of transmissions within a given period of time. For example, if the gateway 420 receives X number broadcast messages from the same beacon within a specified period of time, then the message generating module 428 can instruct the communication unit to transmit the first received message to the server 430 and retain the reminder of the messages until the period of time expires. Thereafter the message generating module 428 transmits a single broadcast.

Server 430 can represent one or more local servers, one or more tracking device servers, or one or more asset management servers. Server 430 can be a web server, a server computer such as a management server, or any other electronic computing system capable of sending and receiving data. In certain embodiments, server 430 is a "cloud" of computers interconnected by one or more networks, where server 430 is a computing system utilizing clustered computers and components to act as a single pool of seamless resources when accessed through network 405. Server 430 can include a location engine 432, an information repository 434 and a cost analysis program 436.

Server 430 can include a communications interface that supports communications with other systems or devices. For example, the communications interface could include a network interface card or a wireless transceiver facilitating communications over the network 405. The communications interface can support communications through any suitable physical or wireless communication link(s). For example, the communication interface can allow the server 430 to receive a message from the gateway 420. In certain embodiments, the server 430 transmits reconfiguration data to the gateway 420. The reconfiguration data allows the gateway 420 to reconfigure one or more beacons 410A-N, when the beacons are configured for wo-way communication. The reconfiguration can include how often a beacon 410A-N transmits a ping 410A-N to the gateway 420.

Location engine 432 identifies the location of a beacon. In certain embodiments, location engine 432 identifies the location of a beacon such as beacon 410A, based on the identification parameter of the gateway that transmitted the message and the signal strength parameter of ping 415A as derived by the gateway 420. Server 430 receives a message from one or more gateways, such as gateway 420. The message can include an identification parameter of the gateway, an identification parameter of beacon, and a signal strength parameter of the ping from the beacon to the gateway 420. For example, when a single gateway 420 receives ping 415A from the beacon 410A, then the location engine 432 identifies the location of the beacon as the location of the gateway 420. In certain embodiments, the location engine 432 identifies a single location of a beacon within a structure, when multiple gateways transmit that includes the same ping 415A from beacon 410A. For example, when multiple gateways receive the same ping 415A from the beacon 410A, it could appear that the beacon is in two locations simultaneously. The signal strength parameter is beneficial to the location engine 432 in this scenario. The location engine can utilize the signal strength parameter to identify a single location for a particular beacon. For instance, when two or more gateways (such as gateway 420A and 420B, not shown) are located within a structure receive ping 415A from the beacon 410A, gateways 420A and 420B include the derived the signal strength parameter in the message. If each gateway 420A and 420B is stationary at a predetermined location, then the location engine 432 compares the received strength parameter from gateway 420A and gateway 420B. Location engine 432 can determine which signal strength parameter is stronger, and assigned the location of the beacon 410A as the location of the gateway that transmitted the message that included the stronger signal strength parameter. That is, once the location engine 432 determines which received message includes the stronger signal strength parameter, the location engine 432 can disregard the weaker message from the respective gateway, and assign the location of the beacon 410A as the location of the gateway that transmitted the message that included the stronger signal strength parameter. This example is discussed further with reference to FIG. 6, below.

In certain embodiments, location engine 432 reduces noise from a received signal. For example, the location engine 432 passes each received signal strength parameter through a low-pass filter in order to eliminate each signal strength parameter that is outside of a threshold. The low-pass filter removes outliers and anomalies that could cause incorrect location results. Once each the signal strength parameters are passes each the low-pass filter, a portion of the received signal strength parameters are averaged together. In certain embodiments, 10 signal strength parameters are averaged together. When location engine 432 averages a portion of the signal strength parameters it generates a standardization factor. Thereafter the location engine 432 compares each signal strength parameter to the standardization factor of the averaged signal strength parameter. By comparing each newly received signal strength parameter to the standardization factor the location engine 432 can identify stronger and weaker signal strength parameters.

For example, when a stronger signal strength parameter is identified, the location engine 432 identifies that the beacon that is associated with that stronger signal strength parameter is closer to the gateway that transmitted the message that included the stronger signal strength parameter. Therefore, the location engine 432 assigns location of the beacon that is associated with that stronger signal strength parameter as the location of the gateway that transmitted the message that included the stronger signal strength parameter.

In another example, when a weaker signal strength parameter is identified, the location engine 432 identifies that the beacon that is associated with that weaker signal strength parameter is further away from the gateway. Location engine 432 can isolate the beacon, such as beacon 410B, that the weaker signal strength parameter is associated with and attempt to identify a gateway that transmitted a message associated with the beacon 410B but with a stronger signal strength parameter. If a message exists, then the location engine 432 identifies that the location of the beacon 410B is the location of gateway that transmitted the message that included the stronger signal strength parameter. If a message does not exist, then the location engine 432 can identify that the location of the beacon 410B is the location of the gateway that transmitted the initial message, identify a null location of the beacon 410B. A null location indicates the beacon is near the gateway but not at the location of the gateway.

In certain embodiments, location engine 432 identifies a location of a beacon based on trilateration. Trilateration is the process of determining absolute or relative locations of points by measurement of distances, using the geometry of circles, or spheres. In certain embodiments, location engine 432 identifies a location of a beacon based on triangulation. Triangulation is the process of tracing and measuring a series or network of triangles in order to determine the distances and relative positions of points spread over an area. In certain embodiments, based on signal strength parameter, trilateration or triangulation the location engine 432 tracks each beacon 410A-N as the beacons 410A-N move throughout the environment.

The information repository 434 can be similar to the information repository 426 of the gateway 420. The information repository 434 represents any structure(s) capable of storing and facilitating retrieval of information (such as data, program code, or other suitable information on a temporary or permanent basis). The information repository 434 can include a memory and a persistent storage. Memory can be RAM or any other suitable volatile or non-volatile storage device(s), while persistent storage can contain one or more components or devices supporting longer-term storage of data, such as a ROM, hard drive, Flash memory, or optical disc. Information repository 434 stores location information of each beacon 410A-N, based on the location of the gateway that transmitted the message as determined by the location engine 432.

In certain embodiments, information repository 434 also stores cost analysis of each beacon. For example, information repository 434 can maintain a log of time stamped events of when a beacon 410A-N enters and leaves a location. Based on the time duration that a beacon 410A-N is located within a single location, cost analysis program 436 can assign a cost associated with the duration of time that the beacon 410A-N is located within the single location. The information repository 434 can also maintain the costs associated with each location.

Cost analysis program 436 analyzes the duration of time that a beacon is located in each location within the structure. Cost analysis program 436 determines a cost associated at each location a beacon is located, based on the cost associated with each room or area of the structure. That is, the cost analysis program 436 can identify actives and assign a cost of each activity based on the time and resources utilized. The cost analysis program 436 provides an indication to controlling spending while improving healthcare access, and efficiency, based on a determination of how and where cost of medical care expenditures occurs. For example, based on the costs associated with each location, cost analysis program 436 can predict revenue and expenditures. Additionally, based on the costs associated with each location, cost analysis program 436 can identify waste and inefficiencies. The identification of waste and inefficiencies can improve patient care.

For example, when a patient goes to a doctor's office, the moment the patient enters the facility the person occupies space that prevents another patient from occupying the same space, such as a seat in the waiting room, an exam room, medical equipment, an imaging device, such as an X-Ray machine, and the like. Each interaction the patient has with an employee or a medical provider is time the employee or medical provider is prevented from assisting another person. Therefore, in order to maximize efficiency and to estimate revenue, approximate costs are associated with each location, and interaction a patient has with a medical provider. For example, if a medical provider sees only one patient a day or fifty (50) patients a day, the medical provider has set expenditures to cover with the income form the patient. For example, the medical provider must pay rent building, salary for himself and staff, medical equipment and tests, and the like. The cost analysis program 436 can derive a quantity of time the medical provider interacts and treats each patient, coupled with the medical equipment used and tests provided, a cost analysis can be performed. The cost analysis program 436 can then notify the medical provider how efficient the medical provider is and whether to expect an income or loss. The cost analysis program 436 can also identify equipment and locations within the structure that are inefficient and provide notifications as to improvements. For example, if the structure has three Magnetic Resonance Imaging (MRI) machines but only two are regularly used, while a single X-Ray machine is continually used, the cost analysis program 436 can indicate that resources are being wasted.

In certain embodiments, the cost analysis program 436 can estimate a cost for each patient and medical provider interaction. Similarly, the cost analysis program 436 can estimate a cost for each patient and the medical equipment as well as each patient and medical test interaction. For example, the cost analysis program 436 can link the identification parameter of a particular beacon with a particular staff member. If the identification parameter of beacon 410B is associated with a particular doctor, then the tracked location and time duration that beacon 410B spends in a particular location are assigned to that particular doctor. In certain embodiments, a status parameter is also associated with the identification parameter of beacon 410B to indicate that the beacon 410B is a doctor. In another example, the cost analysis program 436 can link the identification parameter and the status parameter of a particular beacon with a particular patient. If the identification parameter or the status parameter or both, of beacon 410A is associated with a particular patient then the tracked location and time duration that beacon 410A spends in a particular location is assigned to that particular patient.

Based on the duration of each interaction a cost can be derived based on the salary of a medical provider, and the cost associated with each location. For example, if two beacons are located at the same location, where beacon 410A has a status parameter that indicates the individual is a patient, and the second beacon 410B has a status parameter that indicates the individual is a doctor, the cost analysis program 436 can analyze the time duration that beacon 410A and beacon 410B are located in the same location. Based on the cost associated with the location, and the cost of the doctor as indicated by the beacon 410B, the cost analysis program 436 can derive the cost for the interaction. The cost analysis program 436 can then accrue the time duration that the patient associated with the beacon 410A was located in the waiting room, was located in the exam room without the doctor (the beacon 410B) present, as well as the duration of time of any additional interactions the patient (the beacon 410A) participated in (such as an interaction with a nurse, beacon 410C, medical equipment, and the like).

In certain embodiments, the cost analysis program 436 can determine whether a beacon 410A-N associated with a medical provider is near an electronic device, such as computer 440. In certain embodiments, the cost analysis program 436 is associated with the computer 440 and identifies time duration that specific content is accessed. For example, when a medical provider reviews a patients file, the cost analysis program 436 can associate the time duration that the file is reviewed with the particular patient associated with the file.

In certain embodiments, the cost analysis program 436 can analyze the patient flow and perform a predictive scheduling to optimize time scheduling and management. For example, the cost analysis program 436 can derive patterns based on historical data and predict an allocation of time for various appointments, and procedures to avoid a backlog that causes an increased wait time. The cost analysis program 436 can analyze prior interactions between staff and a particular patient. For example, the cost analysis program 436 can analyze prior appointments of a patient to perform predictive scheduling. For instance, if the cost analysis program 436 identifies that a particular patient takes a long time with a medical provider, then the cost analysis program 436 can suggest or create a longer time block when that particular patient schedules a future appointment with the medical provider. In another example, the cost analysis program 436 can analyze prior interactions between the staff and a particular patient type to perform predictive scheduling. The particular patient type can include an illness, an ailment, demographic data, and the like. In another example, the cost analysis program 436 can analyze data about the medical facility or location to perform predictive scheduling. In another example, the cost analysis program 436 can analyze how fast or efficient particular staff members are when performing a predictive scheduling.

Computer 440 is similar to laptop computer 112 of FIG. 1 and electronic device 300 of FIG. 3. In certain embodiments, the computer 440 can be an electronic device that can access patient files. For example, the cost analysis program 436 can identify a particular file that is accessed and derive a time duration that the file is accessed. In certain embodiments, computer 440 is a user interface that allows a user to view the cost analysis and the medical resource utilization management. The user interface is described in more detail below with respect to FIGS. 7-9B.

Figure 5:
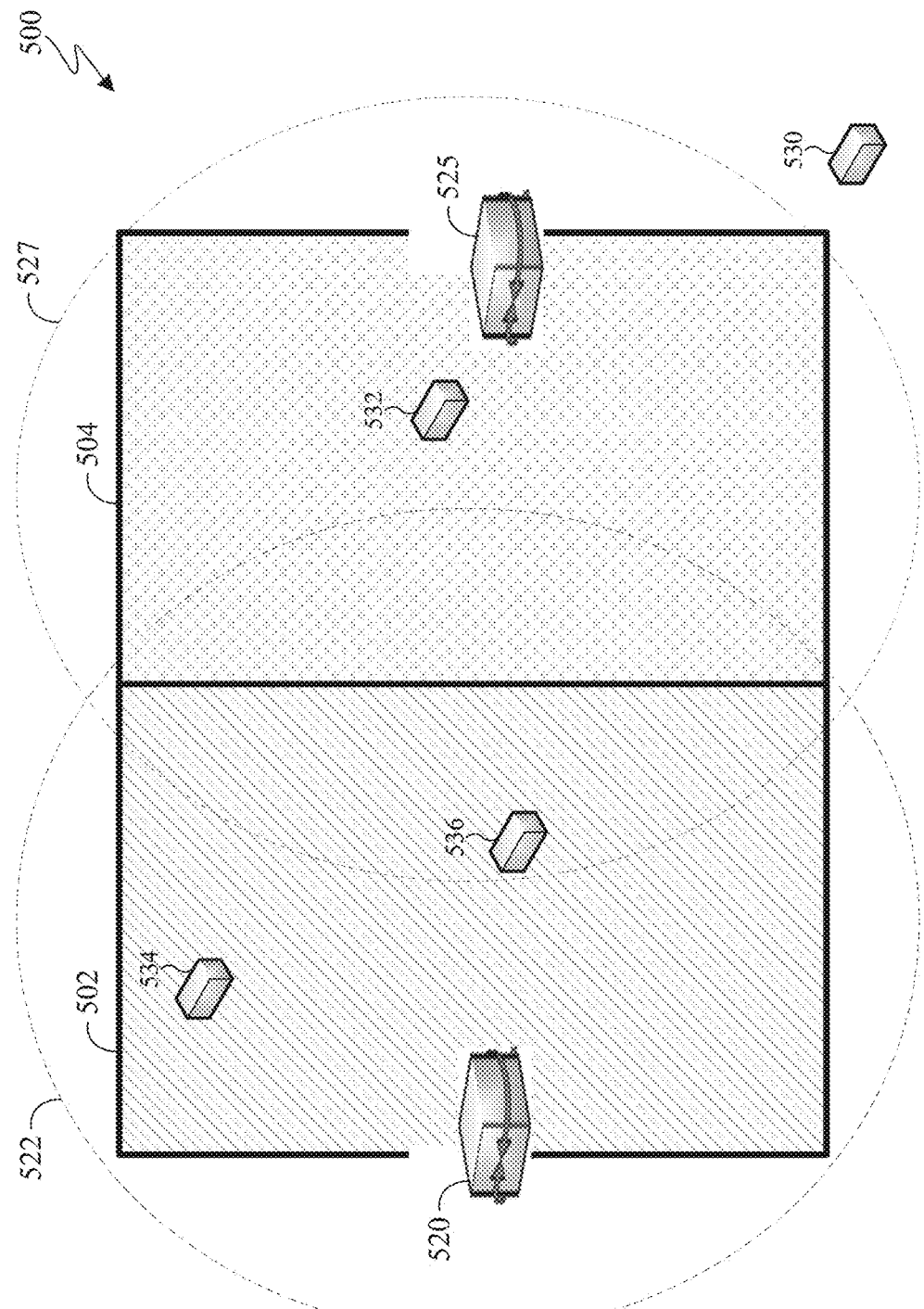
FIG. 5 illustrates an example tracking system in accordance with embodiments of the present disclosure.

FIG. 5 illustrates an example tracking system in accordance with embodiments of the present disclosure. FIG. 5 illustrates environment 500 depicting a tracking and reporting system of beacons with two gateways. The embodiment of the environment 500 shown in FIG. 5 is for illustration only. Other embodiments could be used without departing from the scope of the present disclosure.

Environment 500 illustrates two rooms within a medical facility. Specifically, environment 500 illustrates room 502 and 504. Beacons 530, 532, 534, and 536 are affixed to an individual or medical equipment. Beacons 530-536 are similar to the beacon 118 of FIG. 1, the electronic device 300 of FIG. 3, and the beacons 410A-N of FIG. 4.

Gateway 520 and gateway 525 are located within environment 500. In particular the gateway 520 is located within a room 502 and the gateway 525 is located within a room 504. Gateways 520 and 525 are similar to the gateway 116 of FIG. 1, the electronic device 300 of FIG. 3, and the gateway 420 of FIG. 4. Gateway 520 includes a communication range of 522 for short range communication, such as BLUETOOTH, WI-FI, ZIGBEE, RFID, or other short range signals. Similarly, gateway 525 includes a communication range of 527 for short range communication, such as BLUETOOTH, WI-FI, ZIGBEE, RFID, or other short range signals.

Beacon 530 is located external to rooms 502 and 504 and not within the communication range 522 of gateway 520 or the communication range 527 of the gateway 525. In certain embodiments, if beacon 530 transmits a ping at a predetermined interval, then gateways 520 and 525 do not receive the ping, as beacon 530 is not within the communication range of 522 or 527. Since the ping of beacon 530 is not received by gateway 520 or gateway 525, the beacon 530 cannot be tracked by the cost analysis program 436 of FIG. 4. In certain embodiments, if beacon 530 has an RFID tag, the RFID readers, such as gateways 520 and 525, do not receive the ping as beacon 530 is not within proximity to the gateways 520 and 525. Since the beacon 530 cannot transmit a ping to either gateway 520 or gateway 525 cannot be tracked by the cost analysis program 436 of FIG. 4.

Beacon 532 is located inside room 504 and within the communication range 527 of the gateway 525. The beacon 532 can transmit a ping. The ping can include an identification parameter of the beacon 532. In certain embodiments, the ping can also include a status parameter associated with the beacon 532. The gateway 525 receives the ping while the gateway 520 does not receive the ping since the beacon is within the communication range 527 of the gateway 525. The gateway 525 can determine the signal strength of the received ping from the beacon 532. When the gateway 525 receives the ping, the gateway 525 generates a message. The message includes the identification parameter of the beacon 532, the identification parameter of the gateway 525 and a signal strength parameter of the ping. The gateway 525 then transmits the message to the server, such as server 430 of FIG. 4. In certain embodiments, the beacon 532 can transmit a ping at predetermined intervals. Each time a ping is transmitted a gateway that receives the ping generates a message and transmits the message to the server 430 of FIG. 4. The cost analysis program 436 of FIG. 4 can determine the duration of time that the beacon 532 is located within room 504 since the ping a ping is transmitted at a predetermined interval and a message is generated by the gateway 525 for each received ping. In certain embodiments, the beacon 532 continually transmits a ping. The gateway 525 receives the ping and generates and transmits a message at predetermined intervals to the server 430 of FIG. 4. The cost analysis program 436 of FIG. 4 can determine the duration of time that the beacon 532 is located within room 504 since a message is transmitted from the gateway 525 to the server 430. Upon the cessation of the messages from the gateway 525 that include the identification parameter associated with the beacon 532, the cost analysis program 436 of FIG. 4 can determine an approximate time the beacon 532 left the room 504. Similarly, the cost analysis program 436 can determine an approximate time duration that beacon 532 was within the room 504.

Similarly, beacon 534 is located inside room 502 and within the communication range 522 of the gateway 520. The beacon 534 can transmit a ping. The ping can include an identification parameter of the beacon 534. In certain embodiments, the ping can also include a status parameter associated with the beacon 534. The gateway 520 receives the ping while the gateway 525 does not receive the ping, since the beacon is within the communication range 522 of the gateway 520. The gateway 520 can determine the signal strength of the received ping from the beacon 534. When the gateway 520 receives the ping, the gateway 520 generates a message. The message includes the identification parameter of the beacon 534, the identification parameter of the gateway 520 and a signal strength parameter of the ping. The gateway 520 then transmits the message to the server, such as server 430 of FIG. 4.

Beacon 536 is located inside room 502 and within the communication range 522 of the gateway 520 as well as the communication range 527 of the gateway 525. The beacon 536 can transmit a ping. The ping can include an identification parameter of the beacon 536. In certain embodiments, the ping can also include a status parameter associated with the beacon 536. The gateway 520 and the gateway 525 receive the ping since the beacon 536 is within the communication range 522 of the gateway 522 as well as the communication range 527 of the gateway 525. The gateway 520 can determine the signal strength of the received ping from the beacon 536. When the gateway 520 receives the ping, the gateway 520 generates a message. The message includes the identification parameter of the beacon 536, the identification parameter of the gateway 520 and a signal strength parameter of the ping. The gateway 520 then transmits the message to the server, such as server 430 of FIG. 4. Similarly the gateway 525 also determines the signal strength of the received ping from the beacon 536. When the gateway 525 receives the ping, the gateway 525 generates a message. The message includes the identification parameter of the beacon 536, the identification parameter of the gateway 525 and a signal strength parameter of the ping. The gateway 525 then transmits the message to the server, such as server 430 of FIG. 4. The location engine 432 of the server 430, analyzes the received signal strength parameter of the ping as derived by the gateway 520 with the received signal strength parameter of the ping as derived by the gateway 525. Since the beacon 536 is closer to the gateway 520, the signal strength parameter as derived by the gateway 520 is stronger than the signal parameter as derived by the gateway 525. Therefore, the location engine 432 assigns the location of the beacon 536 within the room 502.

Figure 6:
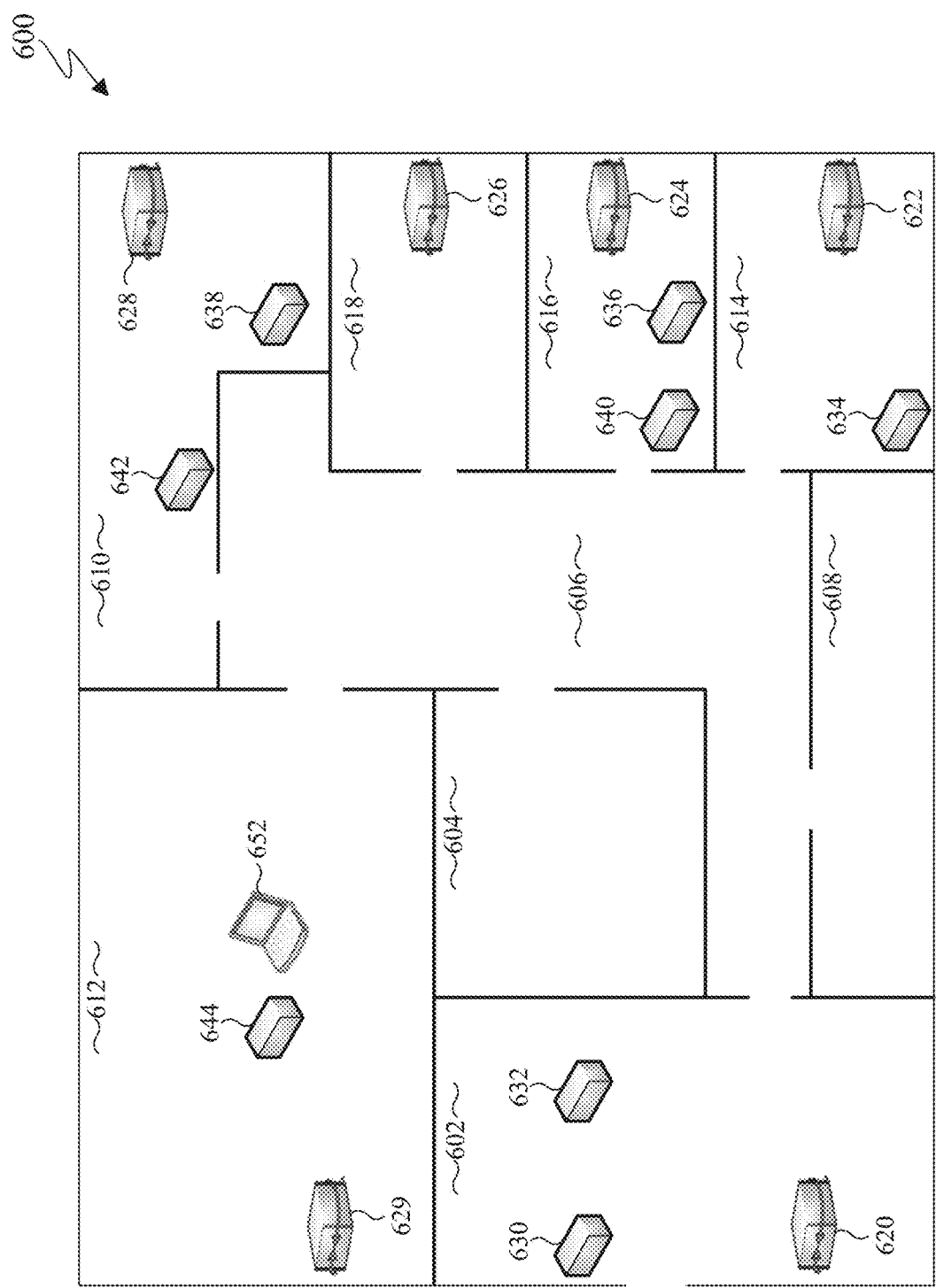
FIG. 6 illustrates an example top view of a tracking system in accordance with embodiments of the present disclosure.

FIG. 6 illustrates an example top view of a tracking system in accordance with embodiments of the present disclosure. FIG. 6 illustrates a medical facility 600 depicting a tracking and reporting system of beacons with many gateways. The embodiment of the medical facility 600 shown in FIG. 6 is for illustration only. Other embodiments could be used without departing from the scope of the present disclosure.

The medical facility 600 illustrates a medical facility with a number of rooms. Specifically, medical facility 600 illustrates nine areas and/or rooms: (i) room 602 is a waiting room; (ii) room 604 is an administrative room; (iii) area 606 is a hallway leading to the various rooms; (iv) room 608 is an empty room; (v) room 610 is a medical imaging room with a stationary X-Ray machine; (vi) room 612 is a file room with a computer; (vii) room 614 is an examination room; (viii) room 616 is an examination room; and (ix) room 618 is an examination room.

Gateways 620, 622, 624, 626, 628, and 629 are located in various rooms in the medical facility 600. Gateways 620-629 are similar to the gateway 116 of FIG. 1, the electronic device 300 of FIG. 3, the gateway 420 of FIG. 4, and the gateways 520 and 525 of FIG. 5. In certain embodiments, rooms where costs can accumulate have a gateway. For example, gateway 620 is located in the room 602, gateway 622 is located in the room 614, gateway 624 is located in the room 616, gateway 626 is located in the room 618, gateway 628 is located in the room 610, and gateway 629 is located in the room 612. In certain embodiments, each room 602-618 can have a gateway (not illustrated). In certain embodiments, communication range of each gateway is limited to each respective room. In certain embodiments, the communication range of each gateway can extend beyond each room. When the communication range of each gateway can extend beyond each room, the signal strength parameter is utilized by the location engine 432 (depicted in FIG. 4) to identify the location of each beacon 630-650.

Beacons 630, 632, 634, 636, 638, are associated with patients. Beacons 640, 642 and 644 are associated with medical providers. Beacon 650 is associated with the computer that is portable. Beacons 630-650 are similar to the beacon 118 of FIG. 1, the electronic device 300 of FIG. 3, the beacons 410A-N of FIG. 4, and beacons 530-536 of FIG. 5. Since beacons 630-650 are associated with equipment and individuals, the beacons 630-650 can be located throughout the medical facility 600. For example, beacons 630 and 632 are associated with patients waiting in the waiting room 602, while beacons 634 and 636 are associated with patients located in the exam rooms 614 and 616, respectively. Similarly, beacon 638 is associated with a patient located in the medical imaging room 610. Beacon 640 is associated with a medical provider that is located in room 616, the beacon 642 is associated with a medical provider that is located in the medical imaging room 610, and the beacon 644 is associated with a medical provider that is located in the file room 612 on the computer.

Beacon 630 transmits a ping with the identification parameter associated with a particular patient. Similarly, the beacon 630 transmits a ping with the identification parameter associated with a particular patient. The gateway 620 receives pings from both the beacon 630 and the beacon 632. In certain embodiments, the gateway 620 generates a message that indicates the identification parameter associated with the beacon 630, identification parameter associated with the beacon 632, the signal strength parameter associated with the beacon 630, signal strength parameter associated with the beacon 632, and the identification parameter of the gateway 620. In certain embodiments, the gateway 620 generates a message each time a ping is received from the beacon 630 and the beacon 632. The message is transmitted to the server 430 of FIG. 4. The location engine 432 identifies the location of each beacon, as the waiting room 602. The cost analysis program 436 then derives a cost associated with beacon 630 and the beacon 632 for the duration of time each beacon remains in the waiting room.

Beacon 634 transmits a ping with the identification parameter associated with a particular patient. The gateway 622 receives pings from the beacon 634. In certain embodiments, the gateway 622 generates a message that indicates the identification parameter associated with the beacon 634, the signal strength parameter associated with the beacon 634, and the identification parameter of the gateway 622. The message is transmitted to the server 430 of FIG. 4. The location engine 432 identifies the location of each beacon, as the exam room 614. The cost analysis program 436 then derives a cost associated with beacon 634 for the duration of time each beacon remains in the exam room 614. If the beacon 634 was located elsewhere in the medical facility 600, the then cost analysis program 436 includes the time duration that the beacon 634 spent in each location.

Beacon 636 transmits a ping with the identification parameter associated with a particular patient. Similarly, the beacon 640 transmits a ping with the identification parameter associated with a particular medical provider. The gateway 624 receives pings from both the beacon 636 and the beacon 640. In certain embodiments, the gateway 624 generates a message that indicates the identification parameter associated with the beacon 636, identification parameter associated with the beacon 640, the signal strength parameter associated with the beacon 636, signal strength parameter associated with the beacon 640, and the identification parameter of the gateway 624. The message is transmitted to the server 430 of FIG. 4. The location engine 432 identifies the location of each beacon, as the exam room 616. The cost analysis program 436 then derives a cost associated with beacon 636 based on the interaction with medical provider (beacon 640) for the duration of time both beacons, 636 and 640 remains in the exam room 616.

Exam room 618 is empty. In certain embodiments, gateway 626 does not transmit any messages as the gateway 626 does not receive any pings. If a ping is received from a nearby beacon, such as beacon 636, 638, 640, or 642, then the gateway 626 generates and transmits a message that includes the identification parameter of the beacon that transmitted the received ping, the identification parameter of the gateway 626, and a derived signal strength parameter of the received ping. The location engine 432 compares the received signal strength parameters from various gateways, such as gateway 624, 626, and 628. When the strongest signal strength parameter is identified the location engine 432 assigns the location of the beacon as the location of the gateway based on the identification parameter of the gateway that transmitted the message.

Beacon 638 transmits a ping with the identification parameter associated with a particular patient. Similarly, the beacon 642 transmits a ping with the identification parameter associated with a particular medical provider. The gateway 628 receives pings from both the beacon 638 and the beacon 642. In certain embodiments, the gateway 628 generates a message that indicates the identification parameter associated with the beacon 638, identification parameter associated with the beacon 642, the signal strength parameter associated with the beacon 638, signal strength parameter associated with the beacon 642, and the identification parameter of the gateway 628. The message is transmitted to the server 430 of FIG. 4. The location engine 432 identifies the location of each beacon as the medical imaging room 610. The cost analysis program 436 then derives a cost associated with beacon 638 based on the interaction with medical provider (beacon 642) and the X-Ray machine located for the duration of time both beacons, 638 and 642 remains in the exam room 610.

Beacon 644 transmits a ping with the identification parameter associated with a particular medical provider. Beacon 650 transmits a ping with the identification parameter associated with the portable computer. The gateway 629 receives pings from the beacon 644 and 650. In certain embodiments, the gateway 629 generates a message that indicates the identification parameter associated with the beacon 644, identification parameter associated with the beacon 650, the signal strength parameter associated with the beacon 644, signal strength parameter associated with the beacon 650, and the identification parameter of the gateway 629. The message is transmitted to the server 430 of FIG. 4. The location engine 432 identifies the location of each beacon, as the file room 612. The cost analysis program 436 can identify when the computer is activated and patient files that are accessed. The cost analysis program 436 then derives a cost associated with each patient that the medical provider associated with beacon 644 reviewed.

Figure 7:
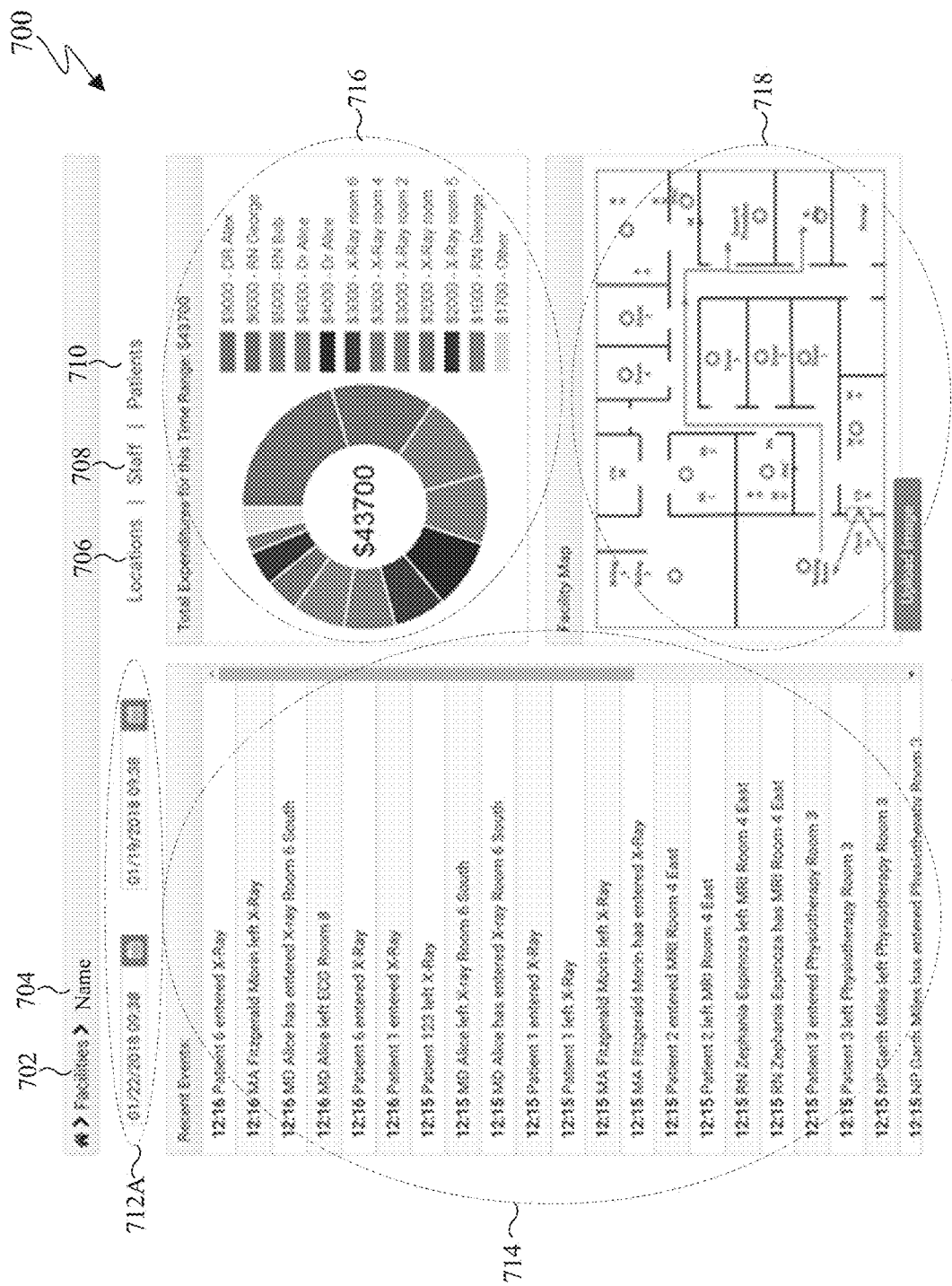
Figure 9A:
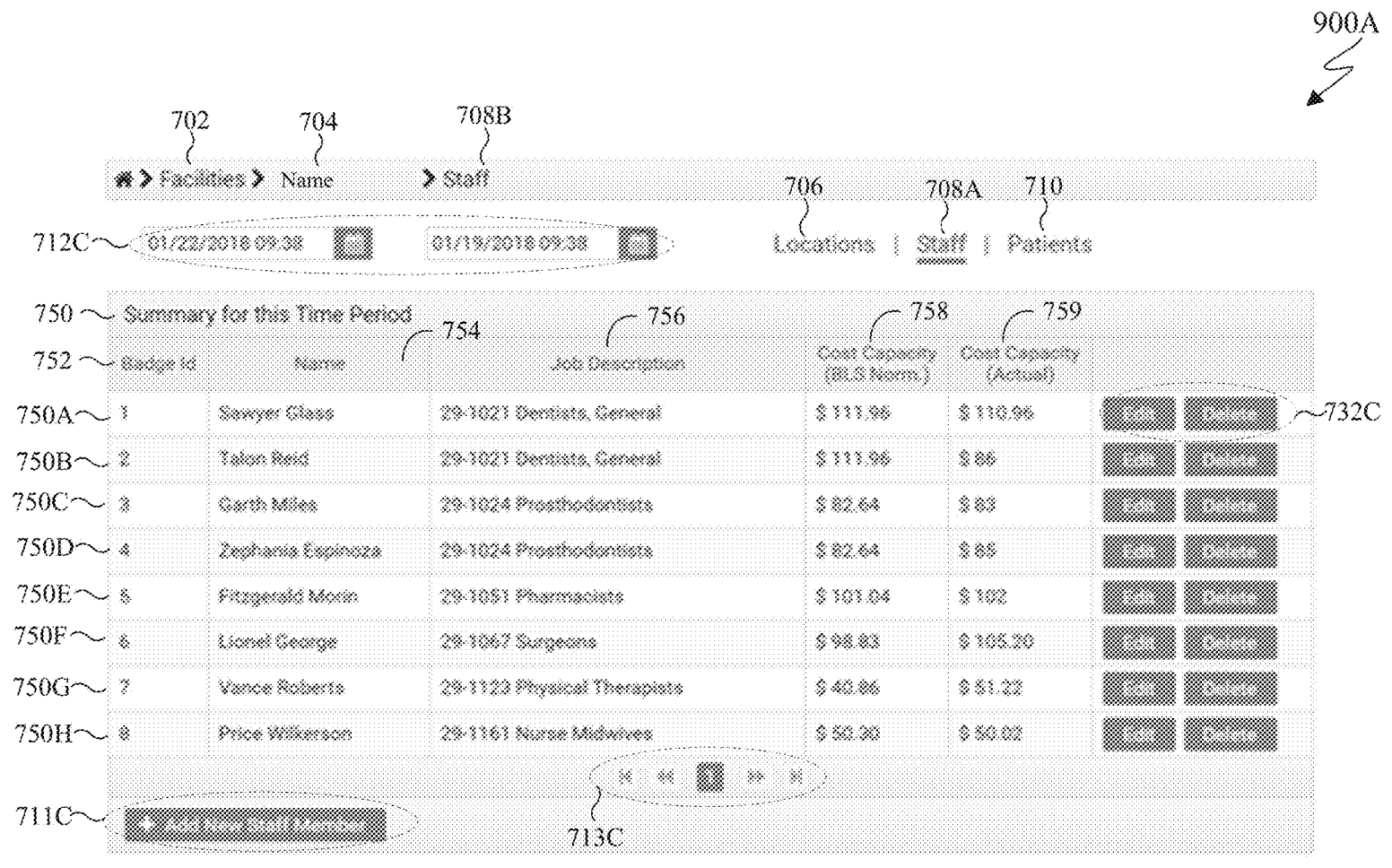
Figure 9B:
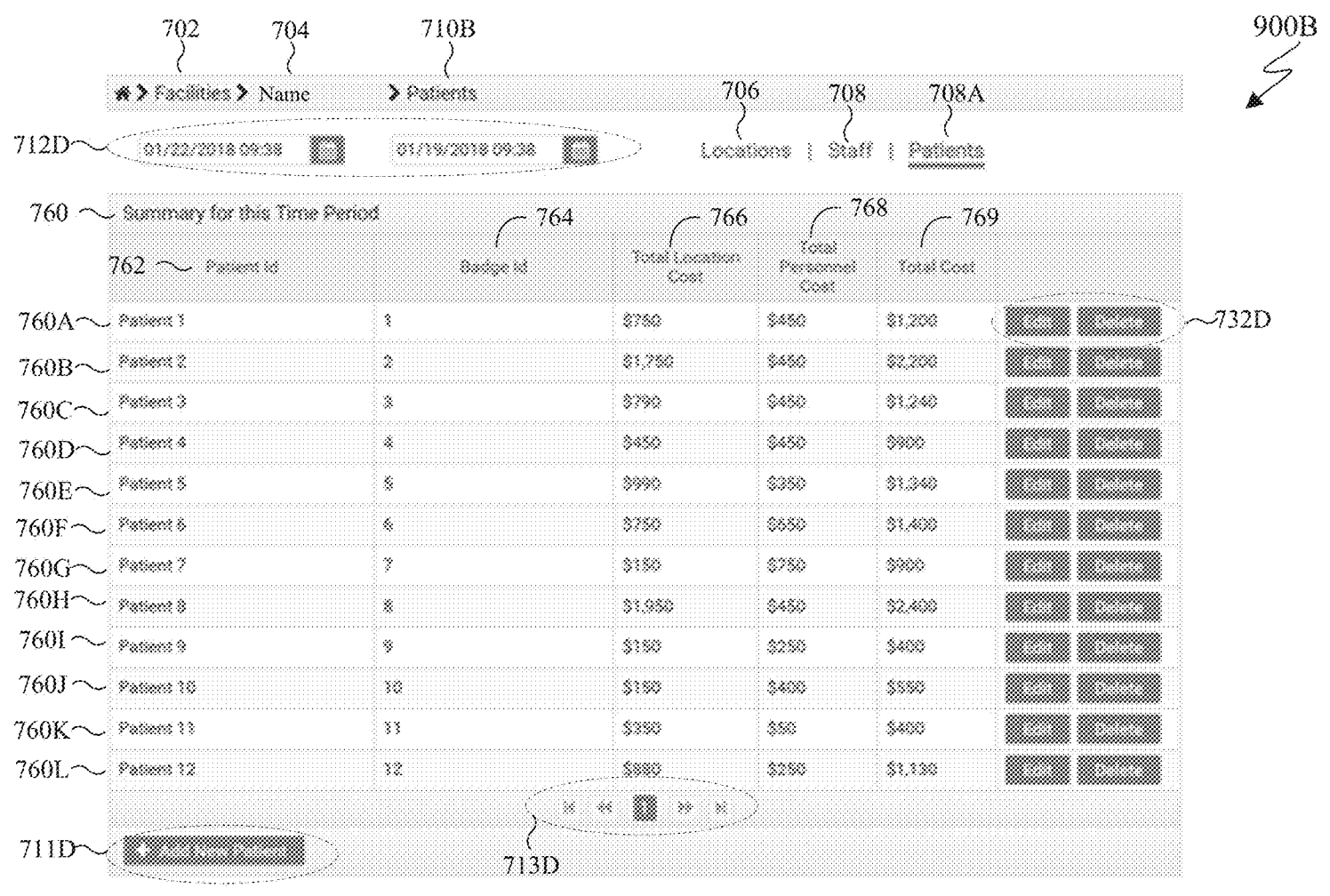

FIGS. 7-9B illustrate example user interface in accordance with embodiments of the present disclosure. FIG. 7 illustrates an example overview of expenditures of a specific facility in accordance with embodiments of the present disclosure. FIG. 8A illustrates specific locations and the costs associated with each location in accordance with embodiments of the present disclosure. FIG. 8B illustrates a summary of expenses of a specific room over a selected time period in accordance with embodiments of the present disclosure. FIG. 9A illustrates a summary of expenditures associated with staff in accordance with embodiments of the present disclosure. FIG. 9B illustrates a summary of expected revenue associated with patients in accordance with embodiments of the present disclosure. The embodiment of the various user interfaces shown in FIGS. 7-9B are for illustration only. Other embodiments could be used without departing from the scope of the present disclosure.

FIG. 7 illustrates user interface 700 depicting an overview user interface screen. Specifically, FIG. 7 illustrates various user selection and customization tools, an events log 714, an expenditure report 716 and a facility map 718. The various user selection and customization tools include a facility list 702, a medical facility name 704, a selection of date and time range 712A, as well as reports based on locations 706, staff 708, and patients 710.

Facility list 702 is a link that returns the user to view multiple linked facilities. In certain embodiments, multiple facilities are linked and allow various users to select and view each facility individually. For example, in a situation where multiple medical facilities are associated with a single management entity, the management entity can select each specific medical facility to review the expenditures and expected revenue. Upon selecting a specific medical facility name 704 the user interface lists the name of the selected medical facility. Medical facility name 704 changes based on the selected medical facility. Similarly, the information displayed on user interface 700 changes based on the selected medical facility name 704.

The date and time range 712A allows a user to select a specific date range to view the events log 714 and expenditure report 716 associated there with. In certain embodiments, the date and time range 712A allows a user to view a minutes, hours, days, weeks, months, yearly, multi-year range, and the like. Based on the date and time range selected via the date and time range 712A, the events log 714 and the expenditure report 716 can change to display the values associated therewith.

The events log 714 lists time stamped activity as detected by each gateway. Each gateway is similar to the gateway 116 of FIG. 1, the electronic device 300 of FIG. 3, the gateway 420 of FIG. 4, the gateways 520 and 525 of FIG. 5, and the gateways 620-629 of FIG. 6. Specifically, the events log 714 lists the identification parameter associated with each beacon indicating when an individual or medical equipment enters or leaves a specific area. Each specific area is designated by the identification parameter of a specific gateway or derived based on the location engine 432 of FIG. 4. The beacons are similar to the beacon 118 of FIG. 1, the electronic device 300 of FIG. 3, the beacons 410A-N of FIG. 4, beacons 530-536 of FIG, and beacons 630-650 of FIG. 6. For example, events log 714 indicates that 'MD Alice entered X-ray room 6 south' at 12:16 and that 'MD Alice left X-ray room 6 south' at 12:15. As indicated in the above example, the gateway in the x-ray room 6 south received a ping from a beacon associated with MD Alice that indicates a time when MD Alice is in the x-ray room. Similarly, the gateway in the x-ray room did not receive a sequential ping to indicate that MD Alice stayed in the x-ray room. As such, the location engine 432 indicates that the MD Alice left the x-ray room. In another example, events log 714 indicates that 'patient 6 enters the X-ray' area and that the 'patient 6 enters X-ray' at 12:16. As indicated in the above example, the gateway in the x-ray room received a ping from a beacon associated with patient 6 that indicates a time when patient 6 is in the x-ray room. Similarly, the gateway in the x-ray room received a sequential ping from the bacon associated with patient 6 that indicates that patient 6 is still within the x-ray room and accruing costs.

The expenditure report 716 depicts a pie graph of the total expenditures for the selected the date and time range 712A. The expenditure report 716 depicts approximate expenditures for medical staff such as medical providers, and nurses as well as specific rooms within the medical facility such as the medical name 704. In certain embodiments, the expenditure report 716 is dynamically generated based on the user selected the date and time range 712A coupled with preset data such as the cost value associated with each medical provider and each room. The expenditure report 716 provides a detailed view of where costs occur, such as a medical imaging location or the waiting room.

In certain embodiments, the cost analysis program 436 of FIG. 4 can determine whether to eliminate a service if it is used seldom. For example, if an X-ray room is used only ten times over the course of a year, then the cost to maintain the X-ray machine and the room it occupies is very expensive. In contrast if an X-ray room is used constantly, the e cost to maintain the X-ray machine and the room it occupies is inexpensive as the costs are spread across each use. That is, if the X-ray machine is not generating patient care but occupying space and resources that could be allocated for patient care, then the cost analysis program 436 of FIG. 4 can determine and provide a notification to a user to reallocate the uses of the specific room.

In certain embodiments, the user interface 700 can also display the waiting time each patient endures while at the medical facility. For example, if a patient waits in the waiting room, waits in the exam room waits prior to seeing the medical provider, the cost analysis program 436 of FIG. 4 can provide a notification to a provider to see the upon when the patient wait time reaches a time threshold. For example, when a patient waits longer than one hour, the medical provider is notified of the wait and to see the patient. In another example, the medical facility can display a wait time on the internet or on a sign outside to notify potential patients of whether the wait is long or short to see a medical provider. In this example, by providing a notice of the wait time allows a potential patient the knowledge of whether to see medical help from this particular facility or see medical assistance at another facility.

In certain embodiments, a medical provider can be notified if the provider is spending too much time with a particular patient. For example, if a medical provider is allotted a predetermined time to spend with each patient, upon the expiration of the allotted time, the cost analysis program 436 of FIG. 4 can notify the medical provider that the time allotted for the particular patient has expired.

In certain embodiments, if a patient is in a room alone, or a patient and provider is in a room alone, the cost analysis is performed. In certain embodiments, if a provider is in a room alone, no cost analysis is performed.

The facility map 718 depicts schematic top view of the medical facility name 704. The facility map 718 depicts a dynamic view of the location on the facility map 718 of the various beacons. The facility map 718 changes based on the selected the date and time range 712A.

Figure 8A:
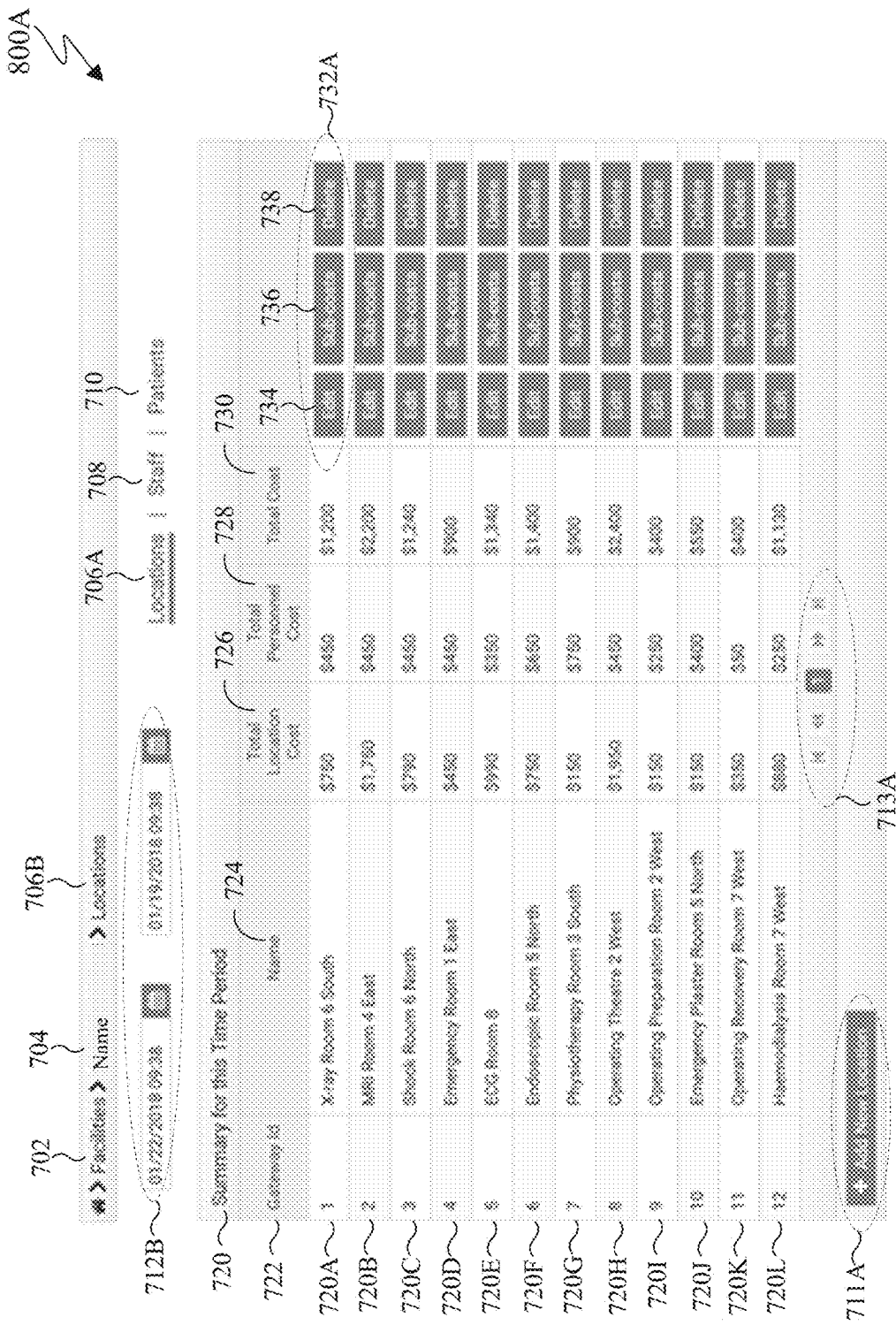

FIG. 8A illustrates user interface 800A listing specific locations and the costs associated with each location. FIG. 8A illustrates various user selection and customization tools and a summary for the time period 720. The various user selection and customization tools include a facility list 702, a medical facility name 704 and the location 706B, a selection of date and time range 712B, as well as reports based on locations 706A, staff 708, and patients 710. Add new location 711A allows a user to program a new gateway in a location as well as set up the costs associated with the new location. Scroll 713A allows a user to scroll and view multiple pages of the summary reports for this time period 720. Facility list 702 is the same facility list 702 of FIG. 7. Similarly, medical facility name 704 is the same medical facility name 704 of FIG. 7. Reports based on locations 706A, staff 708, and patients 710 are similar to the reports based on locations 706, staff 708, and patients 710 of FIG. 7. The date and time range 712B is the same date and time range 712A of FIG. 7. Location 706B indicates that location 706A is currently selected and displayed.

The summary for the time period 720 includes various columns and rows. The columns include a gateway ID 722, a name 724, a total location cost 726, a total personnel cost 728, a total cost 730 and editable icons 732A. The editable icons 732A include edit icon 734, sub-costs icon 736, and delete icon 738. The gateway ID 722 is the gateway identification parameter associated with a specific room. The name 724 is the name of the room that includes a specific gateway. The total location cost 726 is the analyzed cost for each specific location. For example, the total location costs can include costs for the equipment included in the room as well as the size of the room. In certain embodiments, the total location cost 726 can be derived by analyzing the duration of time the specific room is occupied over a period of time. Thereafter the rent can be divided by the size of the room. The total location cost 726 can be utilized to provide a value for a patient in real time, as well as provide an accurate representation of costs attributed to the specific room, but in future usage, and past usage. The total personnel cost 728 is the cost of each medical provider for each specific room. For example, if a room is rarely used, but costs a lot to maintain, the cost analysis program 436 of FIG. 4 can notify the user or provide alternative usages for the specific location or both. The total cost 730 is the total cost that combines the total location cost 726 and the total personnel cost 728. The edit icon 734 allows a user to change the name 724 associated with a specific gateway ID 722. The sub-costs icon 736 allows a user to change the predefined values for a specific room. The sub-costs icon 736 are discussed in greater detail with respect to FIG. 8B. The delete icon 738 allows a user to delete a specific line entry in the summary for the time period 720.

Rows 720A through 720L depict the each gateway located in a specific room within the medical facility. For example, Row 720A indicates that for a gateway ID (722) of 1 is the associated with the room name (726) X-ray room 6 south. The total cost (726) for the room itself is $750 and the total personnel cost (728) is $450. The total cost is $1,200 as it is the addition of the room itself is $750 and the personnel cost is $450.

Figure 8B:
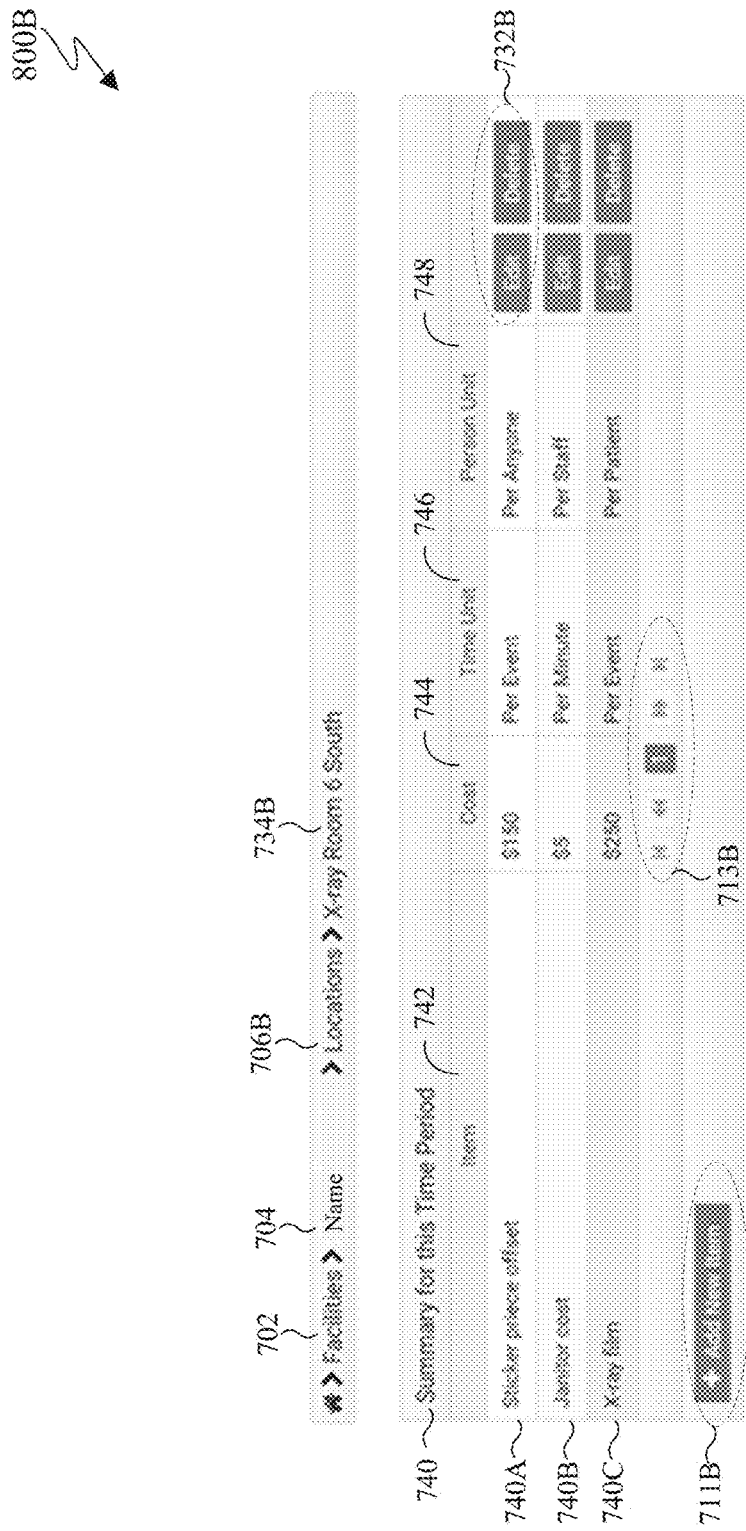

FIG. 8B illustrates user interface 800B listing specific costs associated with a specific location. FIG. 8B illustrates various user selection and customization tools and a summary for the time period 740. The various user selection and customization tools include a facility list 702, a medical facility name 704 and the location 706B, and a location 734B. The location 734B indicates that a user selected the edit icon 734. Specifically, location 734B is the X-ray room 6 south indicating row 720A of FIG. 8A. Facility list 702 is the same facility list 702 of FIG. 8. Similarly, medical facility name 704 is the same medical facility name 704 of FIG. 8.

Add new item 711B allows a user to add a new cost associated with the specific location 734B. Scroll 713A allows a user to scroll and view multiple pages of the summary for this time period 720 report.

The summary for the time period 720 includes various columns and rows. The columns include an item 742, a cost 744, a time unit 746, a person unit, and editable icons 732B. The item 742 indicates a single line item that generates costs associated with the location 734B. The costs 744 indicate the predefined value associated for each specific item. The time unit 746 indicates whether the cost is added as a single item or based on the duration of time a patient is located in the location 734B. The person unit 748 indicates type status parameter of the person that the cost is associated with. The editable icons 732B allow a user to edit or delete a specific row 740A through 740C.

Rows 740A through 740C depict various costs associated with the X-ray room 6 south location 734B. Specifically, rows 740A through 740C illustrate that items 742 include a sticker price offset (740A), janitorial costs (740B), and the costs of an x-ray film (740C). The cost column 744 indicates the predetermined costs associated with each specific item 722. The time unit 746 indicates whether the cost is applied on a time basis or as an event. For example, row 740B indicates that the longer a patient is in the room, the janitor costs increase, as the janitor costs as based on a per-minute interval. In another example, row 740B indicates a non-recoverable cost that the medical facility must spend in order to maintain a clean facility. In another example, 740C indicates that the x-ray film is a set fee, regardless of the duration the patient is located within the room. The person unit 748 indicates who can accrue the costs, such as a staff member of the medical facility, a patient, or both (the staff and the patient).

FIG. 9A illustrates user interface 900A listing specific staff personnel and the costs associated with each staff member. FIG. 9A illustrates various user selection and customization tools and a summary for the time period 750. The various user selection and customization tools include a facility list 702, a medical facility name 704 and the staff 708Ba selection of date and time range 712C, as well as reports based on locations 706, staff 708A, and patients 710. Add new staff member 711C allows a user to program a staff member as well as set up the costs associated facility. Scroll 713C allows a user to scroll and view multiple pages of the summary for this time period 750 report. Facility list 702 is the same facility list 702 of FIG. 7. Similarly, medical facility name 704 is the same medical facility name 704 of FIG. 7. Reports based on locations 706, staff 708B, and patients 710 the reports based on locations 706, staff 708, and patients 710 of FIG. 7. The date and time range 712C is the same date and time range 712A of FIG. 7. Staff 708B indicates that staff 708A is currently selected and displayed.

The summary for the time period 750 includes various columns and rows. The columns include a badge ID 752, a name 754, a job description 756, a costs capacity based on Bureau of Labor Statistics (BLS) Normalization 758, a cost capacity based on actual time duration 759, and editable icons 732C. The badge ID 752 indicates the identification parameter associated with the beacon, that is carried by the particular medical provider or staff member. The name 754 is the name is the medical provider. The job description 756 is the description associated with the medical provider or staff member. The capacity based on BLS Normalization 758 is an average salary for a medical professional as indicated the BLS. In certain embodiments, the BLS Normalization 758 is omitted from the summary for this time period 750. The capacity based on actual time duration 759 is the actual costs accrued by the medical provider or staff member. The editable icons 732C include edit and delete. The edit icon allows a user to preselect various figures and descriptions associated with a particular beacon. For example, the edit icon can allow a user to set the (i) name of the medical provider or the staff associated with the particular beacon, (ii) job description, (iii) salary, (iv) price of the individuals benefit package, (v) hourly wage, (vi) overtime wage, (vii) quantity of paid time off, an (viii) vacation, holiday, of sick time off, to name a few.

In certain embodiments, based on the cost capacity 758 or 759 or both, an efficiency matrix can be assigned to each staff member. Based on the efficiency matrix, an indication is provided as to whether the staff member brings in revenue at or in excess of the costs to retain the staff member.

FIG. 9B illustrates user interface 900B listing specific patents and the costs associated with each patient. FIG. 9B illustrates various user selection and customization tools and a summary for the time period 760. The various user selection and customization tools include a facility list 702, a medical facility name 704 and the patients 710B, a selection of date and time range 712D, as well as reports based on locations 706, staff 708, and patients 710A. Add new patient 711D allows a user to program a new patient that is associated with a certain beacon. Scroll 713D allows a user to scroll and view multiple pages of the summary for this time period 760 report. Facility list 702 is the same facility list 702 of FIG. 7. Similarly, medical facility name 704 is the same medical facility name 704 of FIG. 7. Reports based on locations 706, staff 708, and patients 710A are similar to the reports based on locations 706, staff 708, and patients 710 of FIG. 7. The date and time range 712D is the same date and time range 712A of FIG. 7. Patients 710B indicates that patients 710A is currently selected and displayed.

The summary for the time period 760 includes various columns and rows. The columns include patient ID 762, badge ID 764, total location cost 766, total personnel cost 768, total cost 769 and editable icons 732D. the editable icons include edit and delete functions for each specific row 760A-760L. The patient ID 762 displays an identification of the particular patient. In certain embodiments, the patients name is displayed. In certain embodiments, an alpha-numeric value is associated with each patient for privacy issues. The badge ID 764 indicates the identification parameter associated with the particular beacon that is carried or worn by the particular patient. The total location cost 766 indicates a summary of the location costs accrued by each patient. For example, the total location cost 766 includes costs that a particular patient accrues in each location, such as the waiting room, the exam room, the medical imaging room, and the like. The total personnel costs 768 indicates a summary of the personnel interactions accrued by a particular patient. For example, each time the patient interacts with a staff member, a medical provider, a nurse, and the like, certain costs are attributed based on the duration of the interaction. The total cost 769 is the total cost that combines the total location cost 766 with the total personnel cost 768.

In certain embodiments, the total cost 769 provides an indication as to the costs attributed to a particular patient based on staff member interactions and the time durations spent at particular locations within the medical facility. Based on the total cost 769, the cost analysis program 436 of FIG. 4 can indicate whether the medical facility will make money or lose money from each patient. Further, the cost analysis program 436 can track charges to insurance companies and confirm how much or how little an insurance company paid the medical facility. By comparing the income received from the insurance companies to the projected income as indicated by the total cost 769, the cost analysis program 436 can derive a profit margin for the medical facility in real time.

Figure 10:
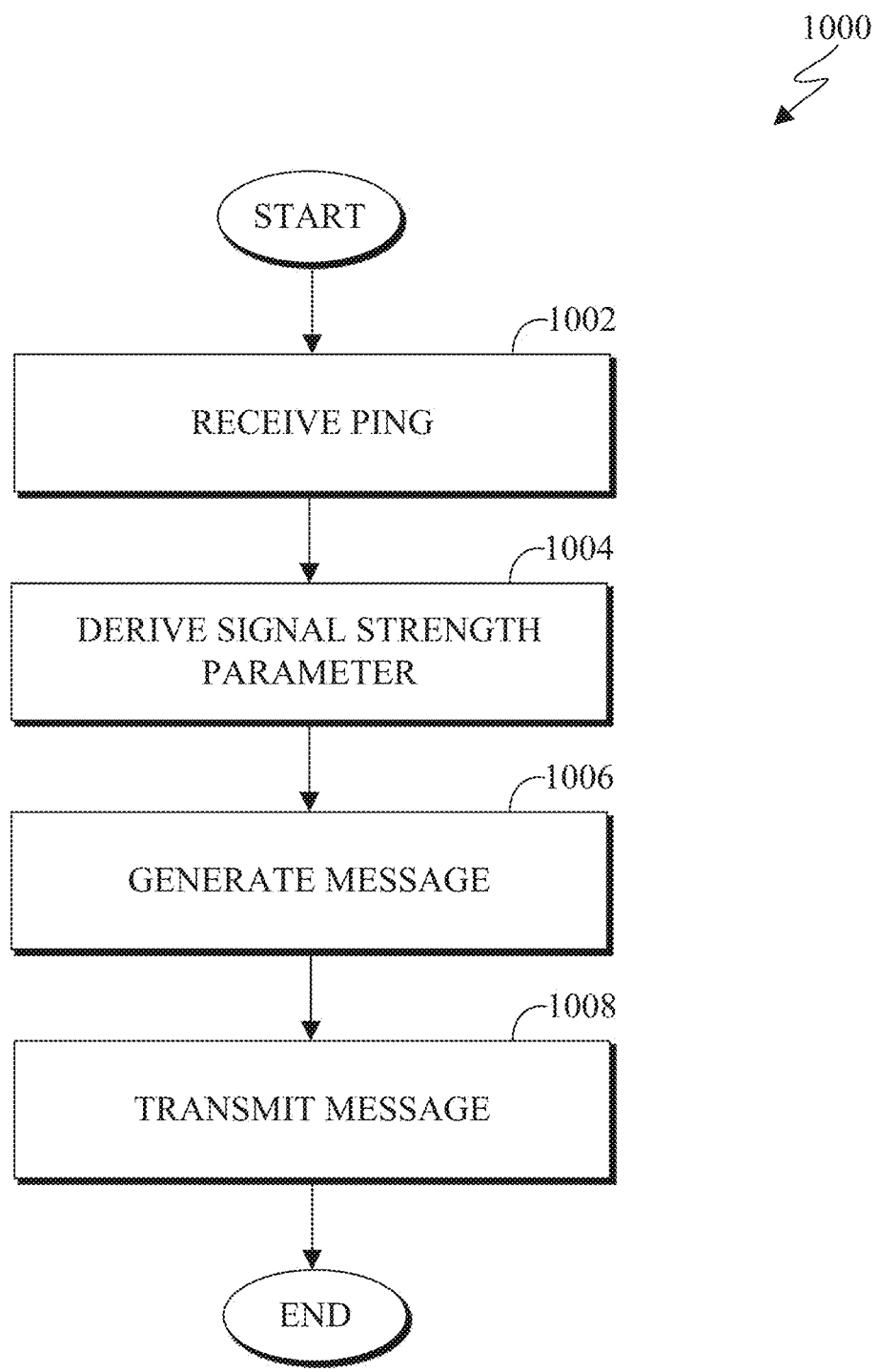
FIG. 10 illustrates a method for transmitting location information by a gateway in accordance with embodiments of the present disclosure.

FIG. 10 illustrates a method for transmitting location information by a gateway in accordance with embodiments of the present disclosure. FIG. 10 does not limit the scope of this disclosure to any particular embodiments. While process 1000 depicts a series of sequential steps, unless explicitly stated, no inference should be drawn from that sequence regarding specific order of performance, performance of steps or portions thereof serially rather than concurrently or in an overlapping manner, or performance of the steps depicted exclusively without the occurrence of intervening or intermediate steps. For ease of explanation, the method receiving a ping with respect to the gateway 116 of FIG. 1, the electronic device 300 of FIG. 3, the gateway 420 of FIG. 4, the gateways 520 and 525 of FIG. 5, and the gateways 620-629 of FIG. 6. The process 1000 is an amplification of the message generating module 428 of FIG. 4, however, the process 1000 can be used with any other suitable system.

In block 1002 the gateway receives a ping from a beacon. The received ping includes an identification parameter associated with the beacon. In certain embodiments, the gateway is configured to receive a plurality of pings from a plurality of beacons at the same or a similar time.

In block 1004 the gateway derives a signal strength parameter associated with the received ping from the beacon. The signal strength parameter indicates how close the beacon is from the gateway.

In block 1006 the gateway generates the message. The message includes the identification parameter associated with the beacon, a second identification parameter associated with the gateway, and the derived signal strength parameter.

In block 1008 the gateway transmits a message to a server when the ping is received. In certain embodiments, the gateway determines whether the received ping was previously received from the beacon within a threshold period. The gateway can also identify whether the signal strength parameter associated with the received ping from the beacon matches a previously derived signal strength parameter associated with the previously received ping from the beacon. When the signal strength parameter associated with the received ping matches a previously received signal strength parameter associated with the previously received ping from the same beacon, and the received ping was previously received from the beacon within the threshold period, the gateway can prevent the message from being transmitted from the gateway to the server.

Figure 11:
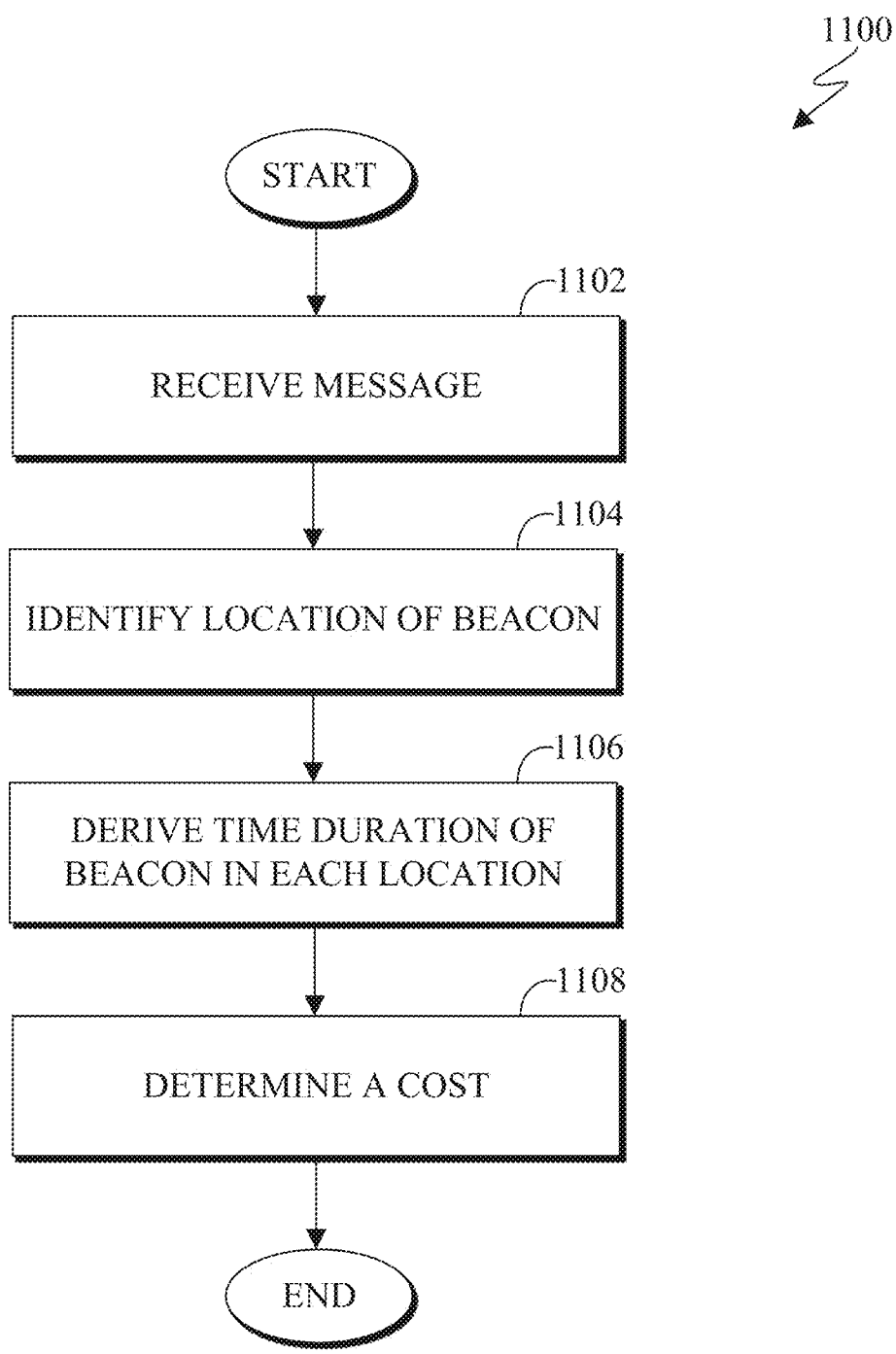
FIG. 11 illustrates a method for determining a cost in accordance with embodiments of the present disclosure.

FIG. 11 illustrates a method for determining a cost in accordance with embodiments of the present disclosure. FIG. 11 does not limit the scope of this disclosure to any particular embodiments. While process 1100 depicts a series of sequential steps, unless explicitly stated, no inference should be drawn from that sequence regarding specific order of performance, performance of steps or portions thereof serially rather than concurrently or in an overlapping manner, or performance of the steps depicted exclusively without the occurrence of intervening or intermediate steps.

For ease of explanation, the method of receiving a location message from a gateway is with respect to the server of 104 of FIG. 1, server 200 of FIG. 2, and the server 430 of FIG. 4. The process 1100 is similar to the cost analysis program 436 of FIG. 4, however, the process 1100 can be used with any other suitable system.

In block 1102 the server 430 receives at least one message from a corresponding number of gateways. Each received message includes a first identification parameter associated with each gateway, and a second identification parameter associated with a beacon. In certain embodiments, each of the at least one message further includes a signal strength parameter associated with a ping from the beacon to the number of gateways. In certain embodiments, the server 430 passes each signal strength parameter through a low-pass filter to eliminate each signal strength parameter that is outside of a threshold. The server 430 then averages the signal strength parameter of a predetermined number of pings. The sever 430 also compares each signal strength parameter to the averaged signal strength to identify the stronger signal strength parameter. In certain embodiments, each of the at least one message further includes a status parameter that associates the beacon to a type of user.

In block 1104 the server 430 identifies a location the beacon is located. The location is one location within an environment, such as a medical facility. In certain embodiments, the server 430 compares the signal strength parameter from each of the at least one message to identify a stronger signal strength parameter. Thereafter the server 430 can assign a location of the beacon as the location of a gateway that sent the message that included the identified stronger signal strength parameter. In certain embodiments, the location of the gateway is predefined and obtained from the first identification parameter associated with each gateway. In certain embodiments, the server 430 also tracks the beacon as the beacon moves through the environment. In certain embodiments, the server 430 identifies each location the beacon is located within the environment based on trilateration. In certain embodiments, the server 430 determines whether a second beacon is located in a similar location that the beacon is located. In response to determining that the second beacon is located in the similar location that the beacon is located, the server 430 updates the determined cost based on a second time duration, when the status parameter of the beacon indicates that the beacon is associated with a patient, and the status parameter of the second beacon indicates that the second beacon is associated with a provider.

In block 1106 the server 430 derives a time duration that the beacon is located in the location. In certain embodiments, the server 430 determines whether a patient file is accessed on an electronic device by a provider, based on receive information about material accessed on the electronic device in real time. The server 430 matches the patient file to the beacon associated with a patient, based on the second identification parameter.

In block 1108 the server 430 determines a cost based on the time duration that the beacon is located in each location. In certain embodiments, each location has a cost value associated with it. In certain embodiments, the server 430 generates a log that maintains an entry when the beacon enters and leaves each location of the environment, where each location has an associated cost based on a type of location. Each of the each of the associated cost of each location is dependent on a status parameter associated with the beacon. In certain embodiments, the status parameters can indicate a patient, a staff employee, a provider, or a technician. In certain embodiments, the server 430 determines the cost associated for each location within the environment, based on the time duration the beacon is located in each location and a predetermined value of equipment in each location. In certain embodiments, the server 430 identifies locations within the environment that produce the lowest cost.

Although the figures illustrate different examples of user equipment, various changes may be made to the figures. For example, the user equipment can include any number of each component in any suitable arrangement. In general, the figures do not limit the scope of this disclosure to any particular configuration(s). Moreover, while figures illustrate operational environments in which various user equipment features disclosed in this patent document can be used, these features can be used in any other suitable system.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the applicants to refer to structures known to those skilled in the relevant art and is not intended to invoke 35 U.S.C. § 112(f).

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A gateway comprising:
    a transceiver configured to:
        receive a ping from a beacon, wherein the received ping includes an identification parameter associated with the beacon, and
        transmit a message to a server when the ping is received; and
    a processor configured to:
        derive a signal strength parameter associated with the received ping from the beacon directed towards a plurality of gateways,
        generate the message that includes the identification parameter associated with the beacon, a second identification parameter associated with the gateway, and the derived signal strength parameter,
        in response to receiving the ping, determine whether a previously received ping was received from the beacon within a threshold period,
        identify whether the derived signal strength parameter associated with the received ping from the beacon matches a previously derived signal strength parameter associated with the previously received ping from the beacon, and
        when the signal strength parameter associated with the received ping matches the previously derived signal strength parameter associated with the previously received ping from the same beacon, and the received ping and the previously received ping from the beacon were received within the threshold period, prevent the transceiver from transmitting the message to the server.

2. The gateway of claim 1, wherein the transceiver is further configured to receive a plurality of pings from a plurality of beacons at a similar time.

3. The gateway of claim 1, wherein the beacon is located in at least one of a stationary position or a mobile situation, and wherein the beacon is associated with a user when the beacon is in the mobile situation, and
    wherein the gateway is located in at least one of a stationary position or a mobile position.

* * * * *